US010179192B2

(12) United States Patent
Brown et al.

(10) Patent No.: US 10,179,192 B2
(45) Date of Patent: *Jan. 15, 2019

(54) INJECTABLE PERIPHERAL NERVE SPECIFIC HYDROGEL

(71) Applicants: UNIVERSITY OF PITTSBURGH-OF THE COMMONWEALTH SYSTEM OF HIGHER EDUCATION, Pittsburgh, PA (US); Cornell University, Ithaca, NY (US)

(72) Inventors: Bryan Nicklaus Brown, Pittsburgh, PA (US); Jonathan Cheetham, Ithaca, NY (US)

(73) Assignees: UNIVERSITY OF PITTSBURGH—OF THE COMMONWEALTH SYSTEM OF HIGHER EDUCATION, Pittsburgh, PA (US); CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/647,744

(22) Filed: Jul. 12, 2017

(65) Prior Publication Data

US 2017/0304499 A1 Oct. 26, 2017

Related U.S. Application Data

(63) Continuation of application No. 14/840,992, filed on Aug. 31, 2015, now Pat. No. 9,737,635, which is a (Continued)

(51) Int. Cl.
*A61L 27/52* (2006.01)
*A61L 27/36* (2006.01)
*A61F 2/04* (2013.01)

(52) U.S. Cl.
CPC ....... *A61L 27/3675* (2013.01); *A61L 27/3604* (2013.01); *A61L 27/3633* (2013.01); *A61L 27/3683* (2013.01); *A61L 27/3687* (2013.01); *A61L 27/52* (2013.01); *A61F 2/04* (2013.01); *A61L 2400/06* (2013.01); *A61L 2430/32* (2013.01)

(58) Field of Classification Search
CPC ..................................................... A61L 24/52
See application file for complete search history.

(56) References Cited

U.S. PATENT DOCUMENTS

| 8,361,503 B2 | 1/2013 | Badylak et al. |
| 2007/0100358 A2 | 5/2007 | Romero-Ortega et al. |
| 2008/0125870 A1 | 5/2008 | Carmichael et al. |

FOREIGN PATENT DOCUMENTS

| WO | WO 2012/002986 A2 | 1/2012 |
| WO | WO 2013/009595 A2 | 1/2013 |

OTHER PUBLICATIONS

Atala (e-biomed: The Journal of Regenerative Medicine. Jul. 2004, 3(1): 1-6).*

(Continued)

*Primary Examiner* — Benjamin J Packard
(74) *Attorney, Agent, or Firm* — Baker Botts L.L.P.

(57) ABSTRACT

The present invention relates to a peripheral nerve-specific hydrogel material, which is deliverable in a minimally invasive fashion, sustains the growth of neurons, and speeds recovery following surgical reconstruction.

5 Claims, 15 Drawing Sheets

Figure 1A:
Figure 1C:
Figure 1B:
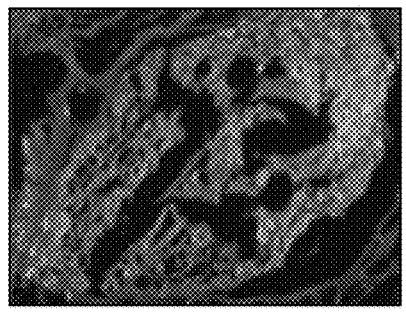
Figure 1D:
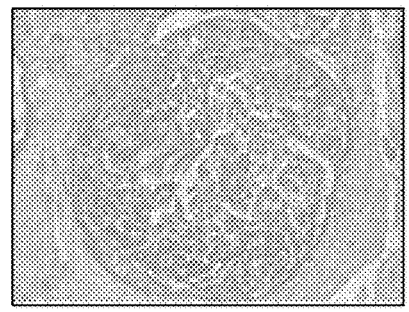
Figure 1E:
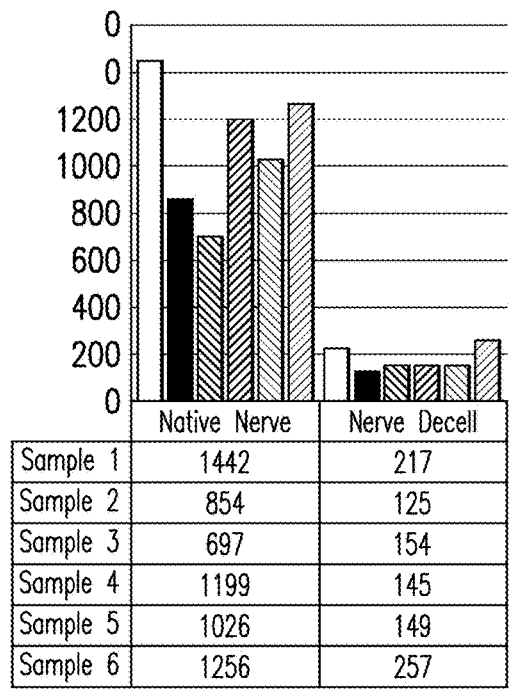
Figure 1F:
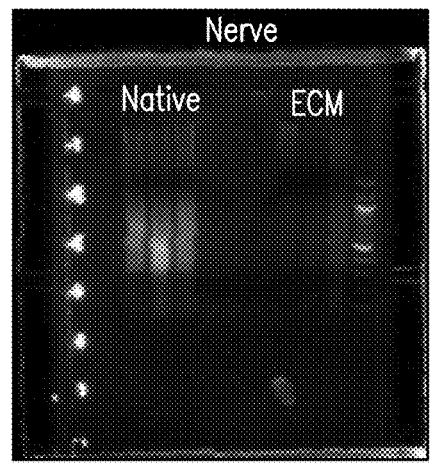
Figures 2A, 2C:
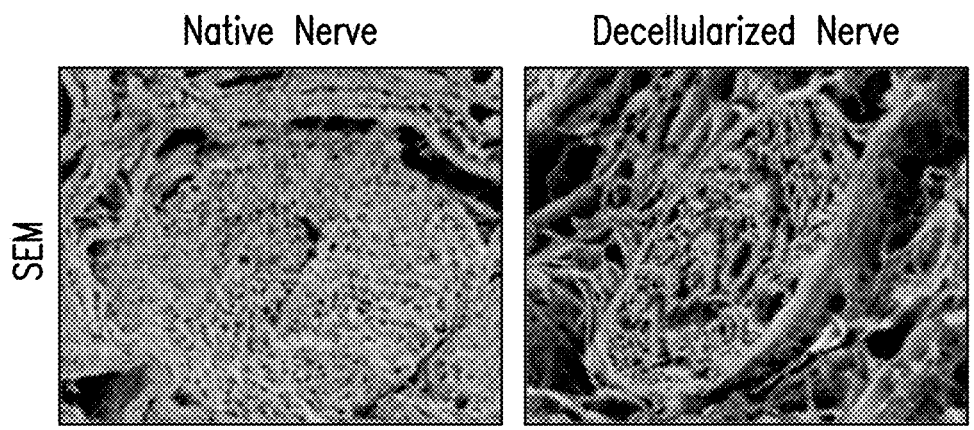
Figures 2B, 2D:
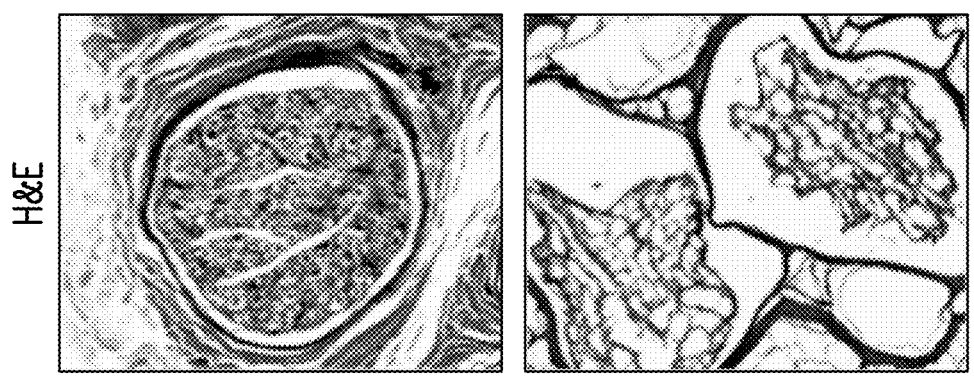

Related U.S. Application Data continuation of application No. PCT/US2014/021065, filed on Mar. 6, 2014.

(60) Provisional application No. 61/773,615, filed on Mar. 6, 2013.

(56) References Cited

OTHER PUBLICATIONS

U.S. Appl. No. 14/840,992, filed Aug. 31, 2015 (Aug. 22, 2017).
U.S. Appl. No. 14/840,992, Jul. 13, 2017 Issue Fee Payment.
U.S. Appl. No. 14/840,992, Apr. 26, 2017 Notice of Allowance.
U.S. Appl. No. 14/840,992, Apr. 7, 2017 Response after Final Office Action.
U.S. Appl. No. 14/840,992, Feb. 8, 2017 Final Office Action.
U.S. Appl. No. 14/840,992, Nov. 4, 2017 Response to Non-Final Office Action.
U.S. Appl. No. 14/840,992, Aug. 8, 2016 Non-Final Office Action.
U.S. Appl. No. 14/840,992, Apr. 13, 2016 Response to Non-Final Office Action.
U.S. Appl. No. 14/840,992, Jan. 13, 2016 Non-Final Office Action.
Affleck et al., "Surgical considerations and controversies in thyroid and parathyroid surgery," Otolaryngol Clin North Am 36:159-187 (2003).
Aynehchi et al., "Systematic review of laryngeal reinnervation techniques," Otolaryngol. Head. Neck. Surg. 143:749-759 (2010).
Badylak, "Decellularized Allogeneic and Xenogeneic Tissue as a Bioscaffold for Regenerative Medicine: Factors that Influence the Host Response," Ann Biomed Eng. 42(7):1517-1527 (2014).
Badylak, "Regenerative medicine: Possibilities and potential," the Singularity Summit (2011). https://www.youtube.com/watch?v=kC1MivfpT9o.
Benjamin, "Vocal cord paralysis, synkinesis and vocal fold motion impairment," Anz J. Surg. 73, 784-786 (2003).
Birchall et al., "Laryngeal Transplantation in 2005: a Review," Am. J Transplant. 6, 20-26 (2006).
Broome et al., "Prevalence of laryngeal paresis in dogs undergoing general anaesthesia," Aust. Vet. J. 78(11), 769-772 (2000).
Brown et al., "Extracellular matrix as an inductive scaffold for functional tissue reconstruction," Transl Res. 163(4), 268-285 (2013).
Brown et al., The Basement Membrane Component of Biologic Scaffolds Derived from Extracellular Matrix. Tissue Eng. 12(3):519-26 (Mar. 2006).
Cheetham et al., "Neuroanatomy of the equine dorsal cricoarytenoid muscle: Surgical implications," Equine Vet. J. 40(1), 70-75 (2008).
Crapo et al., "Biologic scaffolds composed of central nervous system extracellular matrix," Biomaterials. May 2012; 33(13):3539-47.
Crapo, "An overview of tissue and whole organ decellularization processes," Biomaterials 32(12):3233-43 (Apr. 2011).
Crumley, "Laryngeal Synkinesis Revisited," Ann. Otol. Rhinol Laryngol 109, 365-371 (2000).
Deal et al., "Nerve Conduits for Nerve Repair or Reconstruction," J Am Acad Orthop Surg. 20(2):63-8 (Feb. 2012).
DeQuach et al., "Decellularized porcine brain matrix for cell culture and tissue engineering scaffolds," Tissue Engineering: Part A. 17(21-22), 2583-2592 (2011).
DeQuach et al., "Simple and High Yielding Method for Preparing Tissue Specific Extracellular Matrix Coatings for Cell Culture," PLoS ONE 5(9):e13039 (2010).
Dralle, "Intraoperative Monitoring of the Recurrent Laryngeal Nerve in Thyroid Surgery," World J Surg 32(7): 1358-1366 (2008).
Ducharme et al., "Considerations for pacing of the cricoarytenoid dorsalis muscle by neuroprosthesis in horses," Equine Vet. J. 42(6), 534-540 (2010).
Gilbert et al., "Quantification of DNA in biologic scaffold materials," J. Surg. Res. 152(1): 135-9 (Mar. 2009).
Goslin et al., "Changes in the Distribution of GAP-43 During the Development of Neuronal Polarity," J. Neurosci. 10(2), 588-602 (1990).
Hill et al., "Repair of Peripheral Nerve Defects in Rabbits Using Keratin Hydrogel Scaffolds," Tissue Eng. Part A. 17(11, 12), 1499-1505 (2011).
Hudson et al., "Engineering an Improved Acellular Nerve Graft via Optimized Chemical Processing," Tissue Eng. Sep.-Oct. 2004; 10(9-10): 1346-58.
Hudson et al., "Optimized Acellular Nerve Graft Is Immunologically Tolerated and Supports Regeneration," Tissue Eng. Nov.-Dec. 2004; 10 (11-12): 1641-51.
International Search Report dated May 7, 2014 in International Application No. PCT/US2014/021065.
Jansson et al., "An In Vitro Comparison of Cordopexy, Cordopexy and Laryngoplasty, and Laryngoplasty for Treatment of Equine Laryngeal Hemiplegia," Vet. Surg. 29, 326-334 (2000).
Kim et al., "Comparison of Human, Canine, and Ovine Laryngeal Dimensions," Ann. Otol. Rhinol. Laryngol. 113, 60-68 (2004).
Kingham et al., "Reinnervation of Laryngeal Muscles: A Study of Changes in Myosin Heavy Chain Expression," Muscle Nerve 32, 761-766 (2005).
Laccourreye, "Intracordal autologous fat injection for aspiration after recurrent laryngeal nerve paralysis," Eur Arch Otoloaryngol 256:458-461 (1999).
Lee et al., Nerve regeneration with the use of a poly(L-lactide-co-glycolic acid)-coated collagen tube filled with collagen gel. J Craniomaxillofac. Surg. 34, 50-56 (2006).
Lee et al., "Peripheral Nerve Injury and Repair," J Am. Acad. Orthop. Surg. 8, 243-252 (2000).
Lorenz et al., Ansa cervicalis-to-recurrent laryngeal nerve anastomosis for unilateral vocal fold paralysis: experience of a single institution. Ann. Otol. Rhinol. Laryngol. 117(1), 40-45 (2008).
Mackinnon et al., "Clinical Outcome following Nerve Allograft Transplantation," Plast. Reconstr. Surg. 107, 1419-1429 (2001).
Madison et al., "Entubulation repair with protein additives increases the maximum nerve gap distance successfully bridged with tubular prostheses," Brain Res. 447, 325-334 (1988).
Madison et al., "Increased Rate of Peripheral Nerve Regeneration Using Bioresorbable Nerve Guides and a Laminin-Containing Gel," Exp. Neural. 88, 767-772 (1985).
Medberry et al., "Hydrogels derived from central nervous system extracellular matrix," Biomaterials; 34, 1033-40. (2013).
Nagao et al., "Functional characterization of optimized acellular peripheral nerve graft in a rat sciatic nerve injury model," Neurol Res. Jul. 2011; 33(6): 600-8.
Nichols et al., "Effect of motor versus sensory nerve grafts on peripheral nerve regeneration," Exp. Neurol. 190, 347-355 (2004).
Sanders et al., "The Three Bellies of the Canine Posterior Cricoarytenoid Muscle: Implications for Understanding Laryngeal Function," Laryngoscope 103, 171-177 (1993).
Sawkins et al., "Hydrogels derived from demineralized and decellularized bone extracellular matrix," Acta Biomaterialia 9(8), 7865-73. (2013).
Sierpinski et al., The use of keratin biomaterials derived from human hair for the promotion of rapid regeneration of peripheral nerves. Biomaterials 29, 118-128 (2008a).
Smith et al., Ansa-RLN reinnervation for unilateral vocal fold paralysis in adolescents and young adults. Int. J. Pediatr. Otorhinolaryngol. 72, 1311-1316 (2008).
Sobotka et al., "Force Characteristics of the Rat Sternomastoid Muscle Reinnervated with End-To-End Nerve Repair," J Biomed. Biotechnol. vol. 2011, Article ID 173471, 9 pages (2011).
Spector, "Quality-of-life assessment in patients with unilateral vocal cord paralysis," Otolaryngol Head Neck Surg 125(3), 176-182 (2001).
Toba et al., "Regeneration of Canine Peroneal Nerve with the Use of a Polyglycolic Acid-Collagen Tube Filled with Laminin Soaked Collagen Sponge: A Comparative Study of Collagen Sponge and Collagen Fibers as Filling Materials for Nerve Conduits," J Biomed. Mater. Res. 58, 622-630 (2001).

(56) References Cited

OTHER PUBLICATIONS

Triolo et al., "Loss of glial fibrillary acidic protein (GFAP) impairs Schwann cell proliferation and delays nerve regeneration after damage," J. Cell. Sci. 119(19), 3981-3993 (2006).
Van Vlierberghe et al., "Biopolymer-Based Hydrogels as Scaffolds for Tissue Engineering Applications: A Review," Biomacromolecules 12:1387-1408 (2011).
Voytik-Harbin et al., "Identification of extractable Growth Factors from Small Intestinal Submucosa," J Cell Biochem 67:478-491 (1997).
Wang et al., "Contralateral Ansa Cervicalis-to-Recurrent Laryngeal Nerve Anastomosis for Unilateral Vocal Fold Paralysis: A Long-Term Outcome Analysis of 56 Cases," Laryngoscope 121, 1027-1034 (2011).
Wang et al., "Laryngeal Reinnervation Using Ansa Cervicalis for Thyroid Surgery-Related Unilateral Vocal Fold Paralysis: A Long-Term Outcome Analysis of 237 cases," PLoS One 6(4), e19128 (2011).
Wolf et al., "A hydrogel derived from decellularized dermal extracellular matrix," Biomaterials 33(29), 7028-7038 (2012).
Wolf, "Biologic scaffold composed of skeletal muscle extracellular matrix," Biomaterials, 33(10): 2916-25 (2012).
Woodson et al., "Quantitative Assessment of Laryngeal Muscle Morphology After Recurrent Laryngeal Nerve Injury: Right Vs. Left Differences," Laryngoscope 118, 1768-1770 (2008).
Zealear et al., "Synkinesis and Dysfunctional Reinnervation of the Larynx," In: Vocal Fold Paralysis (eds Sulica, L. & Blitzer, A.) Chapter 2, 17-32 (Springer Berlin, Heidelberg, (2006)).
Zealear et al., "The Effects of Chronic Electrical Stimulation on Laryngeal Muscle Physiology and Histochemistry," ORL 62, 81-86 (2000).

* cited by examiner

Empty Conduit          NSECM Conduit

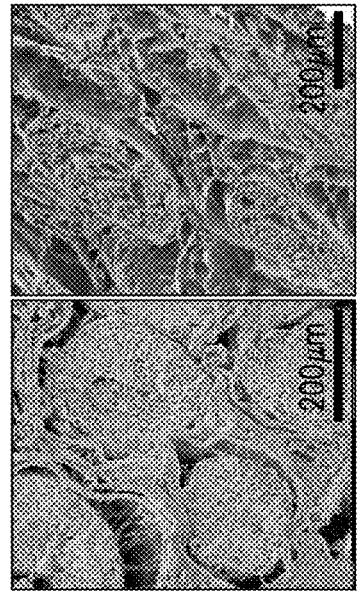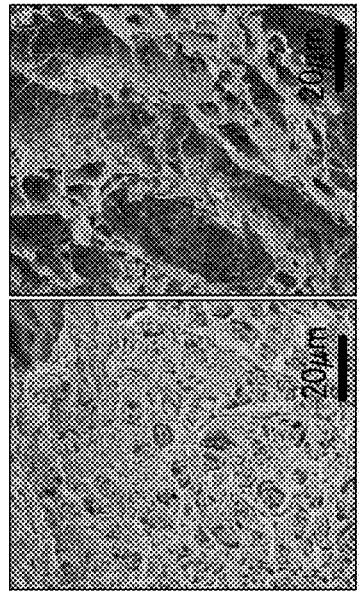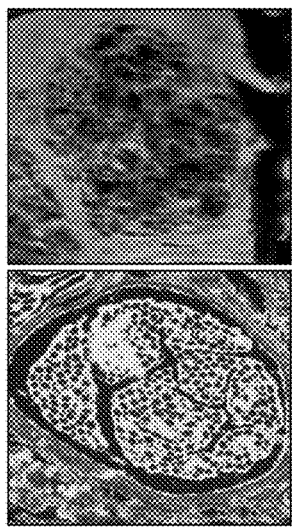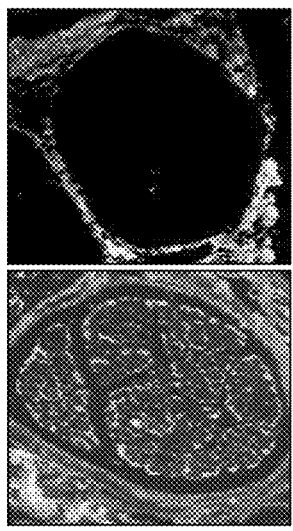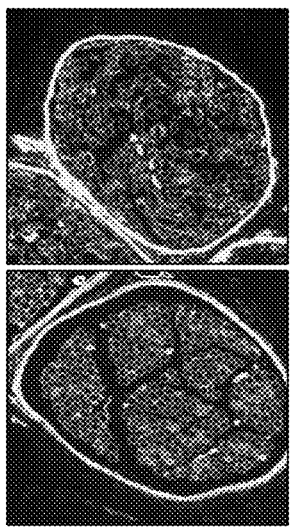

Scale: conduit=
7.5mm long, 3.5mm I.D

INJECTABLE PERIPHERAL NERVE SPECIFIC HYDROGEL

1. PRIORITY CLAIM

This application is a continuation of U.S. patent application Ser. No. 14/840,992, filed Aug. 31, 2015, which is a continuation of International Patent Application No. PCT/US2014/021065, filed Mar. 6, 2014 and claims priority to U.S. Provisional Application Ser. No. 61/773,615, filed Mar. 6, 2013, to all of which priority is claimed and the contents of all of which are incorporated herein in their entireties.

2. INTRODUCTION

The present invention relates to a peripheral nerve-specific hydrogel material, which is deliverable in a minimally invasive fashion, sustains the growth of neurons, and speeds recovery following surgical reconstruction.

3. BACKGROUND OF THE INVENTION

Neuromuscular denervation is a common consequence following peripheral nerve injury. Functional outcomes following repair are often disappointing as the capacity of motor axons to regenerate is decreased with prolonged denervation. Despite advances in microsurgical technique and extensive studies on nerve repair, presently used reinnervation methods produce moderate results and full functional recovery after peripheral nerve injury is seldom achieved.

In cases where anastomosis of the nerve is not possible ("critically sized defect") the current clinical "gold standard" is often nerve autografting. However, autograft harvest is associated with morbidity at the donor site including pain, sensitivity, or loss of sensation and approximately 50% of patients do not regain function following nerve autografting. Allogeneic graft materials have also been suggested. However, fresh allogeneic tissue is subject to an undesirable immune response from the host in the absence of immunosuppression.

For these reasons, a number of alternative approaches have been suggested. These have included both synthetic and biologically derived guidance conduits and hydrogel delivery systems. A wide range of synthetic polymers have been examined for construction of nerve guidance conduits, both with and without cell scale features which either mimic the natural extracellular matrix or provide guidance cues for axonal elongation. However, synthetic nerve guidance conduits are desirably specifically tailored not only to support cellular growth, but also to allow for nutrient diffusion, and to degrade with new tissue formation within the conduit. Long-term implantation of slow degrading synthetic biomaterials is also often associated with a detrimental foreign body type reaction which can hinder recovery.

Various biologically derived materials have been investigated for the fabrication of nerve guidance conduits. The use of a number of individual extracellular matrix (ECM) proteins including collagen, fibronectin, and laminin as well as other biologic materials have been suggested for the fabrication of nerve guidance conduits into simple tubes, or tubes with intraluminal structures intended for guidance of tissue ingrowth. Many of these approaches have been shown to improve outcomes in animal models, although only over relatively short lengths. Others have suggested the use of decellularized allograft nerve tissues as scaffolds for reconstruction of peripheral nerves due to maintenance of the native tissue architecture and functional molecules in their relative tissue specific constituent proportions. However, not all of the proposed decelluarlization methods have been shown to be effective for removal of sufficient cellular content and maintenance of tissue structure, resulting ineffective recovery in some studies.

4. SUMMARY OF THE INVENTION

The present invention relates to a decellularized peripheral nerve specific scaffold which can be formulated into an injectable hydrogel form. It is based, at least in part, on the discovery of a decellularized tissue which substantially lacks immunogenic cellular components but retains sufficient amounts of nerve specific components to be effective at supporting nerve regrowth and reducing or preventing muscular atrophy. In certain non-limiting embodiments, the decellularized tissue scaffold is formulated into a hydrogel through the use of enzymatic degradation. These hydrogels have been shown to be non-cytotoxic to neruons and also support neuronal outgrowth of cultured cells. When injected into injured recurrent laryngeal nerves in a canine model, the hydrogel was shown to improve reinnervation and slow atrophy of the laryngeal muscles as compared to surgical correction without injection.

5. BRIEF DESCRIPTION OF THE FIGURES

FIGS. 1A-F. Confirmation of decellularization. Decellularization was confirmed by the absence of nuclei in DAPI stained sections of decellularized nerve (B). Native nerve shown in (A). Luxol fast blue staining confirmed the removal of potentially immunogenic cellular myelin (D). Native nerve shown in (C). DNA content was assessed by PicoGreen Assay and shown to be reduced by nearly 85% to levels (average 175 ng DNA/mg scaffold dry weight) below those reported for most commercially available ECM scaffold materials (E). DNA was further shown to be reduced on agarose gel analysis (F).

FIG. 2A-D. Electron microscopy (A,C) and histologic evaluation (B,E) of structure. Under SEM, the decellularized sciatic nerves (B) were characterized by an ultrastructure similar to that of native tissue (A). In cross section, distinct nerve bundles can be observed, as can individual structures including the epineureal connective tissues and dense, intact perineurium surrounding each individual nerve bundle. The epineurium is less dense and larger pores are observed than in the native tissue. A number of individual reticular fibers can also be observed. These larger and smaller fibers likely represent the collagen I and III which comprise the majority of the extracellular matrix of the native epineurium. The endoneureal structure is slightly disrupted as compared to native tissue. However, the areas previously occupied by individual nerve fibers (basal lamina) can be observed, and remain highly parallel within the tissue. This is also evident in longitudinal section, where aligned channels and connective tissues can be observed more clearly. Intact blood vessels were also observed in the decellularized samples. These findings were supported by histologic staining. Hematoxylin and eosin stained samples (B,D) in cross section were characterized by a diffuse epineurium, a dense and intact perineurium and basal lamina devoid of cells. Longitudinal sections further confirmed the SEM findings, and were characterized by aligned connective tissue within the epineurium, and patent spaces indicative of basal lamina devoid of axonal and supporting cells.

Figure 3:
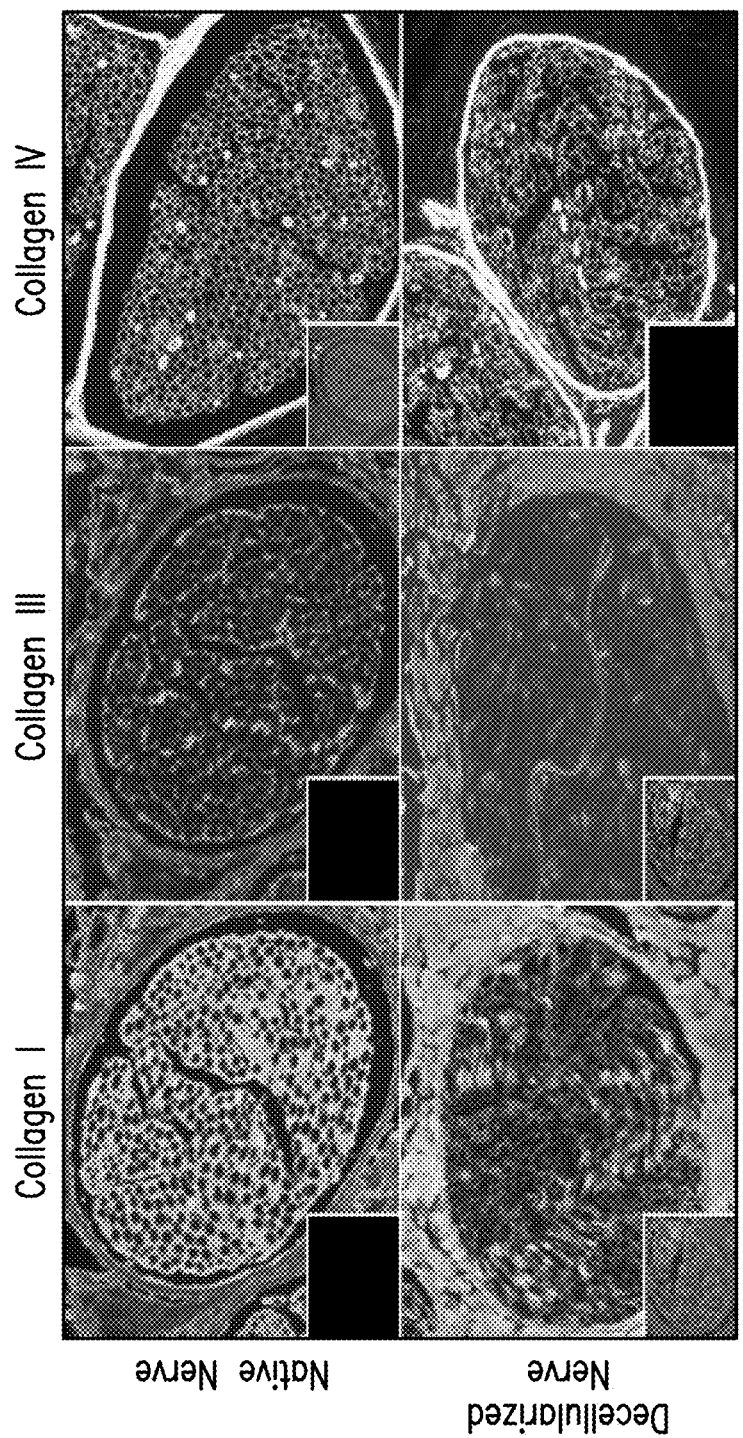
Figure 4A:
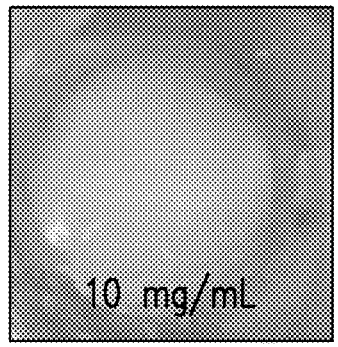
Figure 4B:
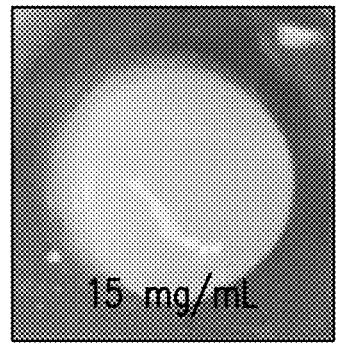
Figure 4C:
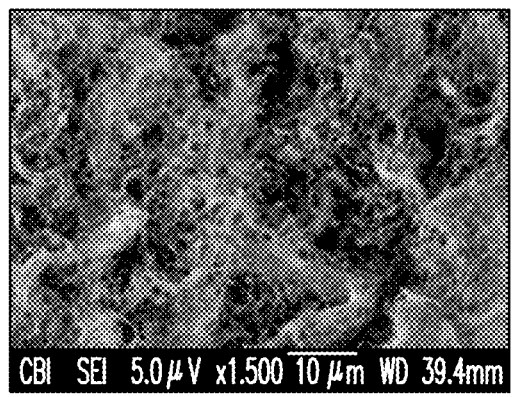
Figure 4D:
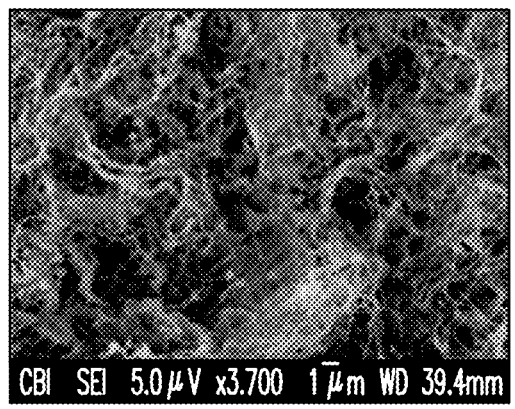

FIG. 3. Maintenance of specific ECM components. Immunolabeling confirmed the presence of collagen I, III, and IV within the decellularized samples. These components were observed present in an architecture that resembled that of native nerve. However, the intensity of the staining was less and the architecture slightly disrupted as compared to native tissue.

FIG. 4A-D. Hydrogel formation. Enzymatically digested samples of the decellularized nerve described above were neutralized and reconstituted at multiple concentrations and placed into an incubator at physiologic temperature to induce gelation (A,B). Hydrogel formation was improved at concentrations of 12.5+mg/mL. SEM of hydrogels demonstrates a highly fibrous architecture of hydrogel (C,D).

Figure 5A:
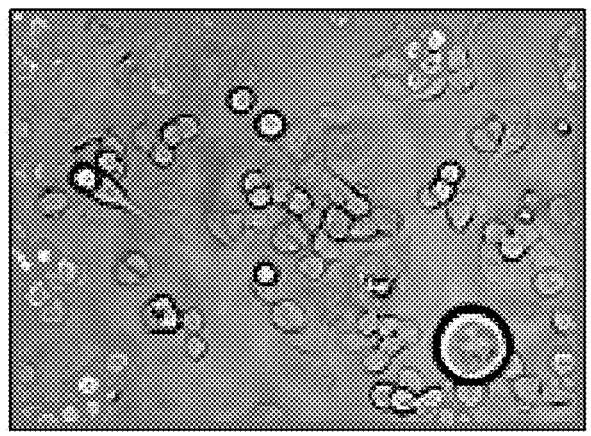
Figure 5B:
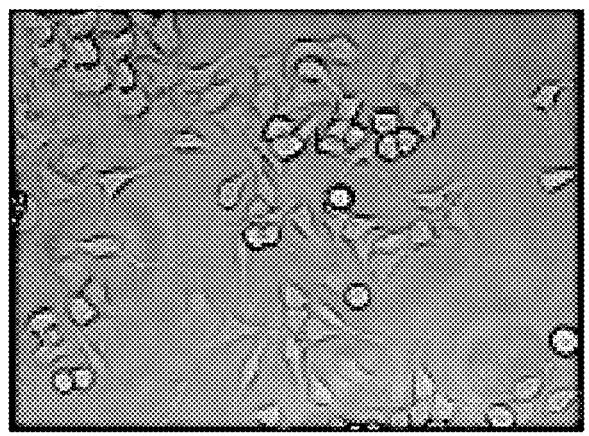
Figure 5C:

FIG. 5A-C. Nerve ECM digest is non-cytotoxic and promotes neurite outgrowth. When a neuronal cell line was exposed to the digested ECM, neurite extension was seen as early as Day 1 of culture and continued with increasing extension length for up to 3 days in culture. Longer time periods were not examined. Day 0 (A), Day 1 (B), and Day 3 (C) are shown. Neurite extension following exposure to ECM digest was equivalent to results obtained for neurons exposed to neurite outgrowth media (positive control) suggesting the decellularized nerve hydrogel promotes nerve outgrowth.

Figure 6:
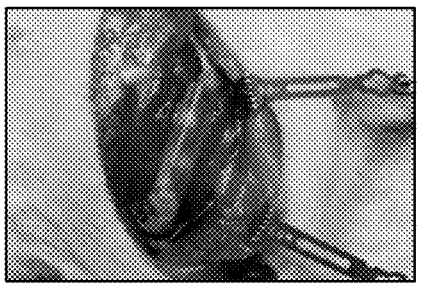
Figure 6:
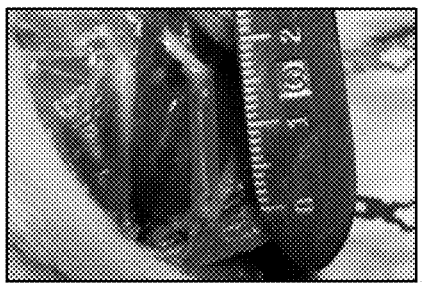
Figure 6:
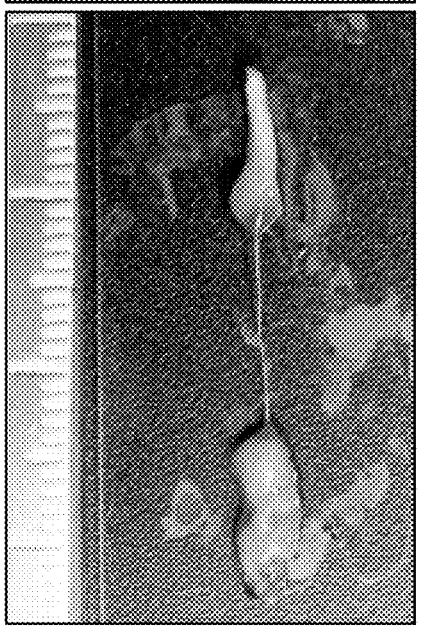
Figure 6:
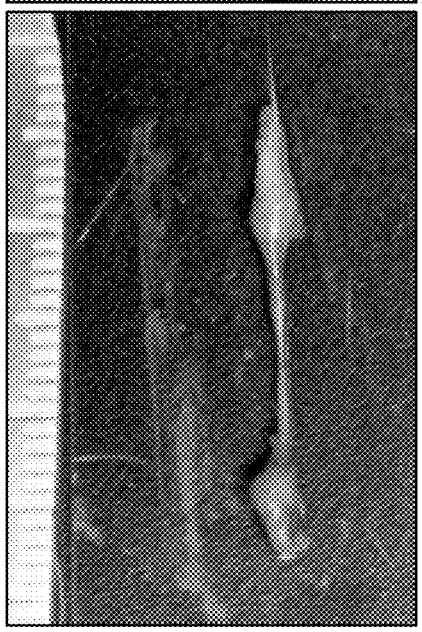

FIG. 6. Gross morphology of control (left panel) and treated (right panel) sciatic nerves at 21 days post-surgery. There was little to no tissue growth within empty conduit compared to conduit filled with nerve specific (NS)-ECM. Top panels show conduit before explant and bottom panels show tissue formed within the conduit (conduit removed).

FIG. 7A-G. Qualitative assessment of decellularization. Few cells remained while maintaining much of the structure. The Tubular structure remained after decellularization. (A & B) H&E, Native and Decell, (C & D) Luxol Fast Blue for Myelin, Native and Decell, and (E & F) Dapi stain, Native and Decell, (G) Picogreen assay for DNA content shows dsDNA content of the decellularized tissue (158.07±34.53 ng/mg) was significantly decreased as compared to native tissues (1043.65±291.20 ng/mg).

Figure 8K:
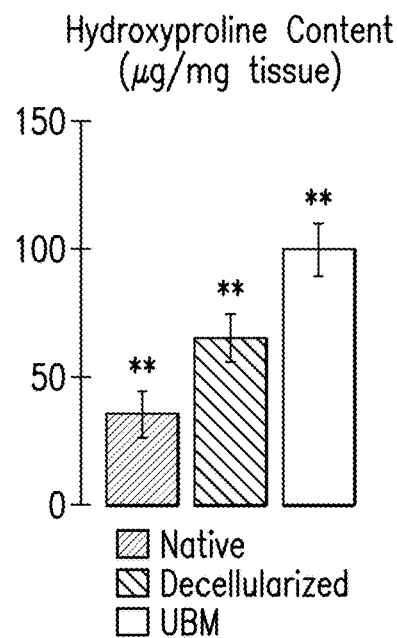
Figure 8L:
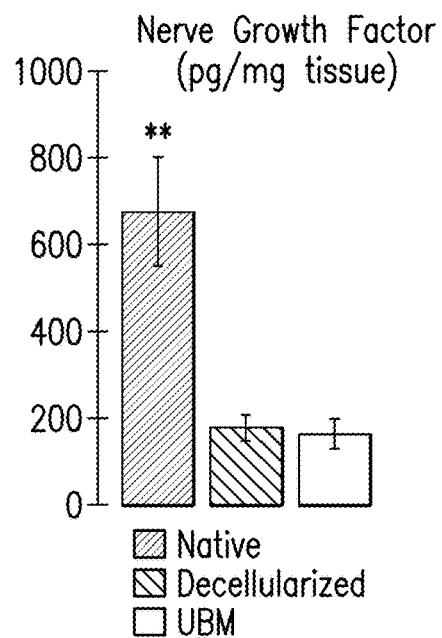
Figure 8M:
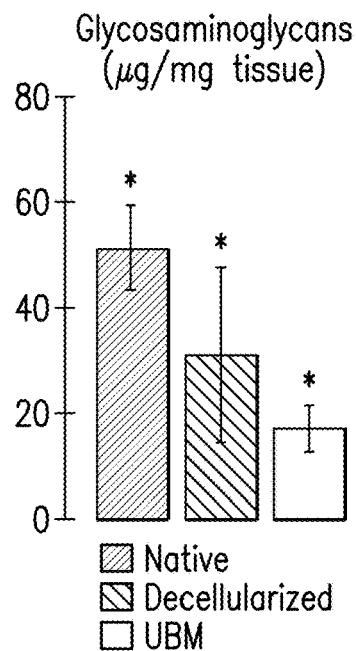
Figure 8N:
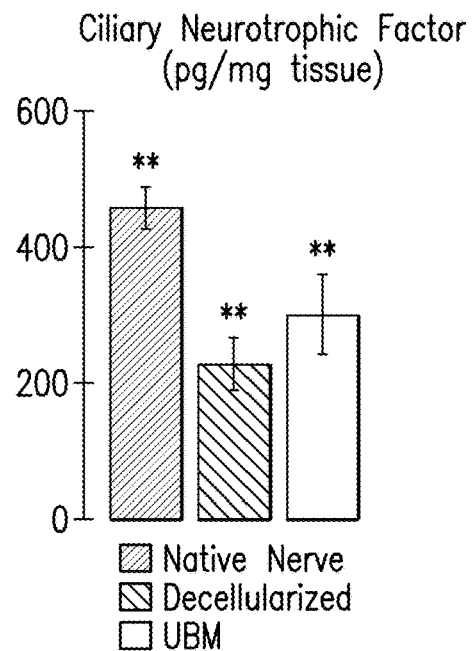
Figure 9A:
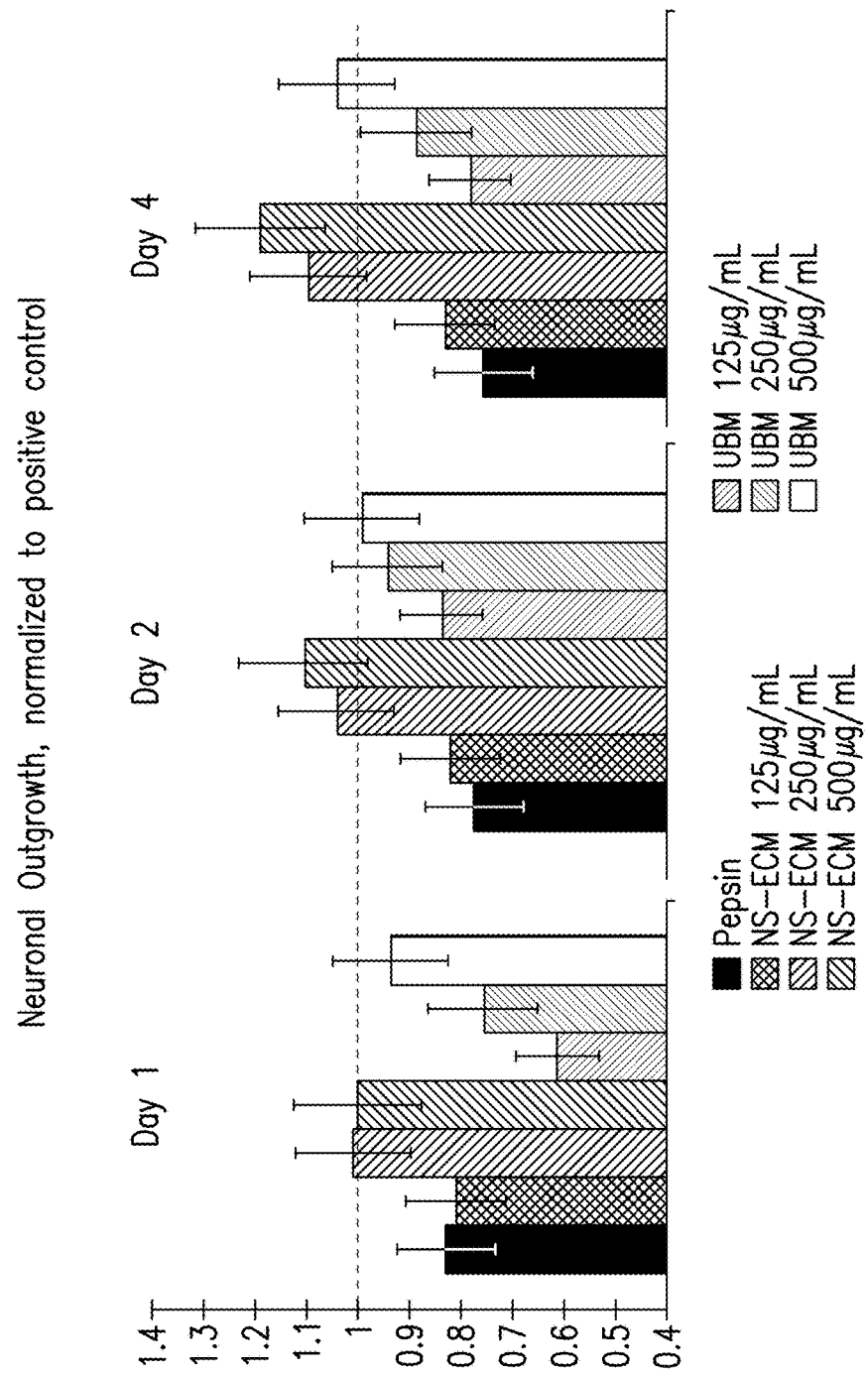
Figure 9B:
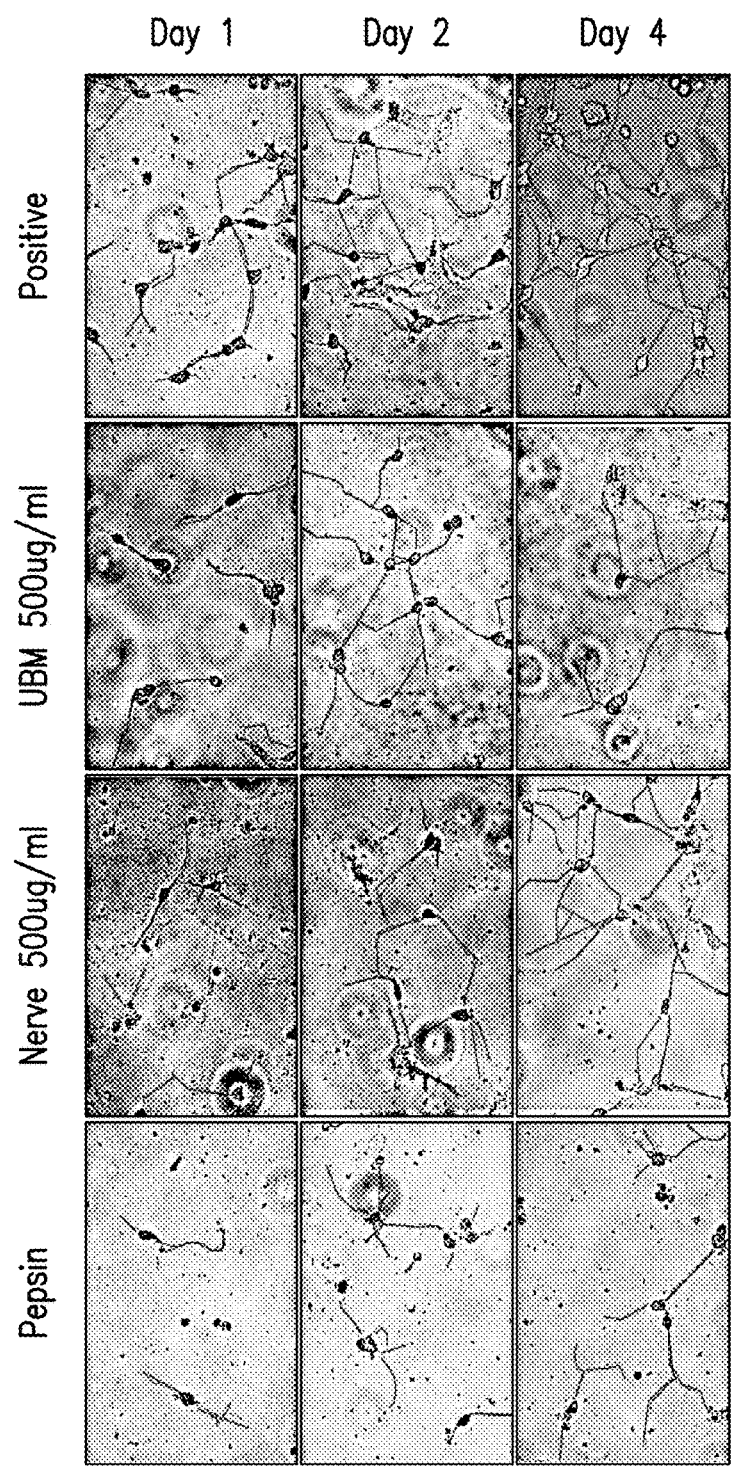
Figure 9C:
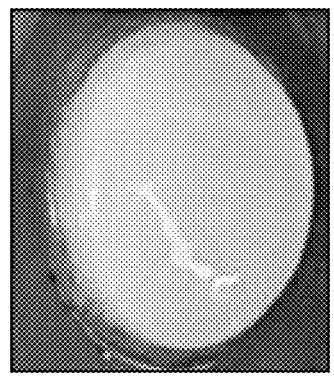
Figure 9D:
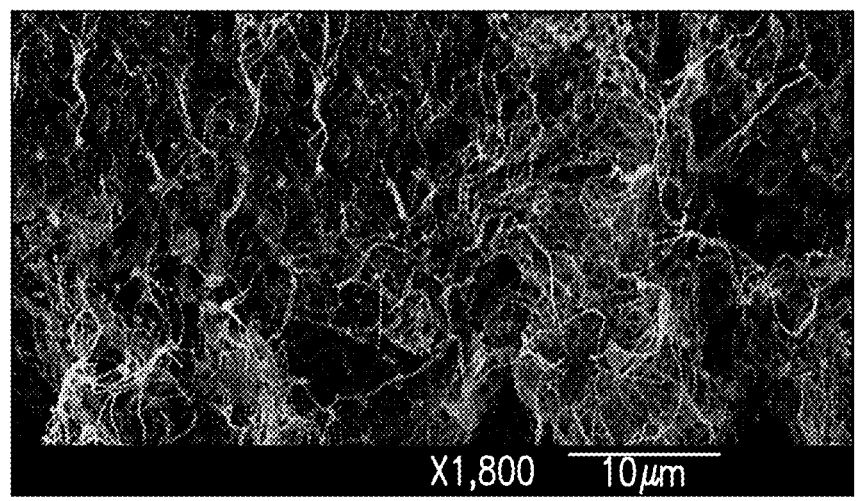

FIG. 8A-N. Immunohistology, Electromicroscopic and Biochemical analysis for major extracellular matrix molecules. Native and decellularized nerve tissue stained for (A) Collagen I native, (B) Collagen I NS-ECM, (C) Collagen III native, (D) Collagen III NS-ECM, (E) Collagen IV native, (F) Collagen IV NS-ECM. (G and H) Electromicroscopic appearance of intact nerve. (I and J) Electromicroscopic appearance of decellularized nerve. (K-N) Biochemical assays for hydroxyproline, GAG, NGF, and CNTF content.

FIG. 9A-D. (A) Degradation products of decellularized nerves were introduced at different concentrations to primary neurons over four days. (B) Images from neurite outgrowth with pepsin control and positive (b27 supplement) control and nerve and urinary bladder matrix (UBM) at 500 ug/ml. (C and D) Digested decellularized nerve products were formed into a stable gel. Concentration of gel was 15 mg/mL.

FIG. 10A-D. (A) Intraoperative photo of silicon conduit placement after anastomosis of transected recurrent laryngeal nerve (RLn). (B) Compound muscle action potential amplitude measured at the vocalis muscle after super-stimulation of the RLn. (C) Duration between stimulation of the RLn and recorded action potential at the vocalis muscle. (D) Muscle fiber diameter of the posterior cricoarytenoid muscle. All three measurements were taken after 6 months of recovery, post-surgery.

Figure 11:
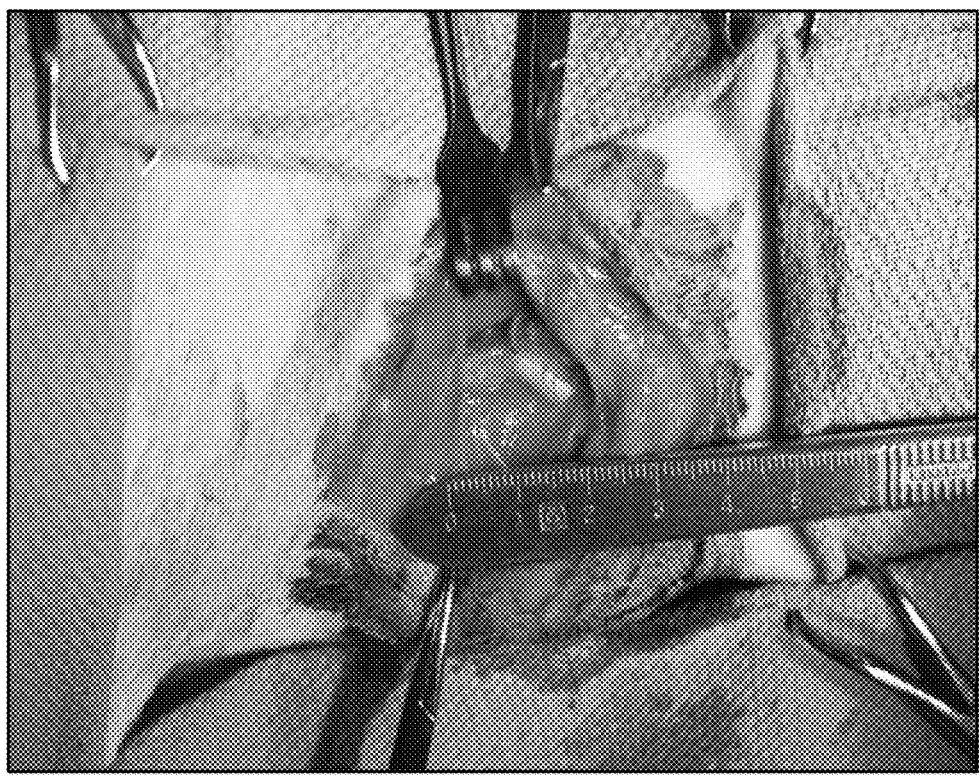

FIG. 11. NS-ECM injection. NS-ECM was injected within a silicone conduit to support the grafting of the first cervical nerve to the Rln three months post-injury.

6. DETAILED DESCRIPTION OF THE INVENTION

The present invention relates to a peripheral nerve-specific hydrogel material, which is deliverable in a minimally invasive fashion, that is capable of sustaining the growth of neurons and promoting recovery following surgical reconstruction.

In certain non-limiting embodiments, the present invention provides for a nerve tissue-specific decellularized scaffold and hydrogel for peripheral nerve repair, wherein the scaffold material is derived through the decellularization of a peripheral nerve. In non-limiting embodiments, as exemplified below, a portion of the peripheral nerve may be used to form the scaffold. Said peripheral nerve can be obtained from an autologous or a non-autologous source. In one non-limiting embodiment, said peripheral nerve is obtained from a non-autologous source, such as syngenic, allogeneic or xenogenic source which may be of the same or a different species, such as a human or a non-human animal such as a non-human primate, a dog, a cat, a horse, a cow, a sheep, a goat, or a pig. In non-limiting embodiments, the peripheral nerve is a sciatic nerve, femoral nerve, ulnar nerve, median nerve, musculocutaneous nerve, common peroneal nerve, sural nerve or other motor or sensory nerve. In one specific non-limiting embodiment. the peripheral nerve is an equine sciatic nerve.

The scaffold material retains sufficient nerve specific components so as to effectively support nerve repair. The hydrogel form of the scaffold is injectable at sites of nerve repair, and has been shown effective in promoting nerve functional recovery and in reducing muscular atrophy when used at sites of nerve repair in the recurrent laryngeal nerve.

In certain non-limiting embodiments, the present invention provides one or more of the following advantages:
 a method of decellularization which reduces immunogenic cellular components to a minimal level while retaining a large number of peripheral nerve-specific components;
 a hydrogel which is peripheral nerve specific (the inventors are not aware of any other peripheral nerve specific decellularized hydrogel, and data supports the concept that tissue specific scaffolds generate a superior response to generic xenogeneic scaffolds); and
 the material has been demonstrated to promote recovery following injection around surgically reconstructed peripheral nerves in a clinically relevant large animal model.

Accordingly, in certain embodiments the invention provides for a hydrogel comprising a decellularized peripheral nerve scaffold that has been enzymatically degraded to form a hydrogel, wherein the hydrogel promotes peripheral nerve repair. In specific non-limiting embodiments, the hydrogel is injected into or comprised in a conduit, as is known in the art to facilitate or guide the regrowth of nerves. The conduits can be absorbable or non-absorbable. Suitable conduits include, but are not limited to, three types of bioabsorbable conduit that have been approved by the US Food and Drug Administration: conduits constructed of collagen, polyglycolic acid, or caprolactone (Deal 2012).

In a non-limiting embodiment, peripheral nerve extracellular matrix (ECM) may be prepared as follows. A peripheral nerve, for example a sciatic nerve, may be harvested and then frozen for at least 16 h at −80° C. The epineurium may be stripped and the tissue quartered longitudinally and cut into lengths of <5 cm. Decellularization may then be performed as previously described by Medberry (2013). For example, the decellularization process may comprise a series of agitated washes: water (type 1), 0.02% trypsin/0.05% EDTA (60 min at 37° C.), 3.0% Triton X-100 (60 min), water rinse (type 1, repeated until agitation no longer produced bubbles), 1M sucrose (15 min), 4.0% sodium deoxycholate (60 min), 0.1% peracetic acid/4% ethanol (120 min), 1×PBS (15 min), water (15 min), water (15 min), 1×PBS (15 min). Following treatment samples may be frozen (−80° C.) and then lyophilized.

In non-limiting embodiments, enzymatic degradation product and ECM hydrogel may be prepared as follows. Lyophilized scaffold materials may be powdered using a Wiley mill through a 40 mesh screen. The powdered material may be solubilized at a concentration of 20 mg/mL in a solution containing 2.0 mg/mL pepsin in 0.01 N HCl at a constant stir rate for 48 h. The ECM digest solution may then be frozen at −20° C. until use. Enzymatic digestion may be stopped by raising the pH of the solution to 7.4 using NaOH and diluting the solution to the desired concentration with PBS. Gellation of the neutralized digest may be induced by increasing the temperature of the gel into the physiologic range 37° C.

Alternative decellularization processes and methods of generating ECM degradation product are known in the art and may be used where the resulting product is at least 50% or at least 80% or at least 90% as peripheral nerve specific as the hydrogel prepared according to the method set forth above. Other potential variations upon the hydrogel may include addition of bioactive components or therapeutic agents. Therapeutic agents within the hydrogel can be used in various ways. The therapeutic agent can be released from the hydrogel. For example, an anti-inflammatory drug can be released from the hydrogel to decrease an immune response. Additionally or alternatively, the therapeutic agent can be substantially remain within the hydrogel. For example, a chemoattractant can be maintained within the hydrogel to promote cellular migration and/or cellular infiltration into the hydrogel. At least one therapeutic agent can be added to the hydrogel before it is injected into a conduit. Suitable therapeutic agents can include any substance that can be coated on, embedded into, absorbed into, adsorbed onto, or otherwise attached to or incorporated onto or into the hydrogel that would provide a therapeutic benefit to an intended recipient. Suitable therapeutic agents include, but are not limited to, antimicrobial agents, growth factors, emollients, retinoids, and topical steroids. Each therapeutic agent may be used alone or in combination with others. In one non-limiting embodiment, the hydrogel comprises neurotrophic agents or cells that express neurotrophic agents, which hydrogel is used for nerve repair.

The therapeutic agent can be a growth factor, such as a neurotrophic or angiogenic factor, which optionally may be prepared using recombinant techniques. Suitable growth factors include, but are not limited to, basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

Additionally or alternatively, the therapeutic agent can be an antimicrobial agent. Suitable antimicrobial agents include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

The therapeutic agent can be an anti-inflammatory agent. Suitable anti-inflammatory agents include, but are not limited to, a NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; and an anti-clotting agent, such as heparin. Other drugs that may promote wound healing and/or tissue regeneration may also be included.

Another variation may include polymeric components or additional biologic components in addition to the hydrogel. Another variation would include the hydrogel which has been seeded with cells prior to or at the time of injection. The cells that are integrated may remain after the hydrogel has fully disintegrated within the conduit. However, the microintegrated cells may also be merely cells that act as precursors to the final tissue that is formed when the hydrogel has fully degraded. Cells may be autologous (obtained from the intended recipient), from an allogeneic or xenogeneic source or from any useful cell line, including, but not limited to, stem cells or precursor cells (cells that can differentiate into another cell type) that are capable of cellular growth, remodeling, and/or differentiation. Suitable cells that can be incorporated onto or into the hydrogel include, but are not limited to, stem cells, precursor cells, smooth muscle cells, skeletal myoblasts, myocardial cells, endothelial cells, fibroblasts, chondrocytes and genetically modified cells. Various commercially available cell lines include Clonetics® Primary Cell Systems (Lonza Group, Inc., Switzerland), ATCC.

Non-limiting examples of uses of the hydrogel of the invention include the following.

In certain non-limiting embodiments, the hydrogel may be injected within a conduit to be used to bridge critically sized defects. A "critically sized defect", as used herein, is a defect not amenable to joining anastamosis, for example, but not limited to, a gap of at least about 10 mm, or a gap of at least about 15 mm, or a gap of at least about 20 mm.

In certain non-limiting embodiments, the hydrogel may be used to support direct peripheral nerve repair either soon after injury (acute) or after a period of delay (chronic), e.g., at least about two weeks delay, at least about 1-month delay, at least about 2-months delay, at least about 3-months delay, at least about 4-months delay, at least about 5-months delay, at least about 6-months delay, at least about 12-months delay, or at least about 24-months delay, and/or up to about 2-years delay, up to about 3-years delay, up to about 4-years delay, or up to about 5-years delay. Delays often occur prior to nerve repair to allow soft tissue and orthopedic injuries to heal.

In certain non-limiting embodiments, the hydrogel may be used to support a peripheral nerve graft used to reinnervate a denervated nerve either soon after injury (acute) or more commonly after a period of delay (chronic), e.g., at least about two weeks delay, at least about 1-month delay, at least about 2-months delay, at least about 3-months delay, at least about 4-months delay, at least about 5-months delay, at least about 6-months delay, at least about 12-months delay, or at least about 24-months delay, and/or up to about 2-years delay, up to about 3-years delay, up to about 4-years delay, or up to about 5-years delay. In one non-limiting embodiment, the delay is about 3 months.

In certain non-limiting embodiments, the hydrogel may be used to bridge critical gaps in peripheral nerves. These gaps could arise as a result of traumatic injury or iatrogenic injury during surgery for example tumour removal.

7. EXAMPLES

Example 1

Equine sciatic nerve was harvested at the Cornell University College of Veterinary Medicine following euthanasia of adult animals for reasons unrelated to the sciatic nerve. The tissue was then frozen for at least 16 h at −80° C. The epineurium was stripped and the tissue was quartered longitudinally and cut into lengths of <5 cm. Decellularization was then performed as previously described by Medberry (2013). Briefly, the decellularization process consisted of a series of agitated washes: water (type 1), 0.02% trypsin/0.05% EDTA (60 min at 37° C.), 3.0% Triton X-100 (60 min), water rinse (type 1, repeated until agitation no longer produced bubbles), 1M sucrose (15 min), 4.0% sodium deoxycholate (60 min), 0.1% peracetic acid/4% ethanol (120 min), 1xPBS (15 min), water (15 min), water (15 min), 1xPBS (15 min). Following treatment samples were frozen (−80° C.) and then lyophilized.

Enzymatic degradation products were generated as previously described. Briefly, lyophilized scaffold materials were powdered using a Wiley mill through a 40 mesh screen. The powdered material was solubilized at a concentration of 20 mg/mL in a solution containing 2.0 mg/mL pepsin in 0.01 N HCl at a constant stir rate for 48 h. The ECM digest solution was then frozen at −20° C. until use in subsequent experiments. Enzymatic digestion was stopped by raising the pH of the solution to 7.4 using NaOH and diluting the solution to the desired concentration with PBS. Gellation of the neutralized digest is induced by increasing the temperature of the gel into the physiologic range 37° C.

Example 2

Animals (Sprague Dawley rats, female 240-280 g) were anesthetized and an approach made through the lateral thigh to the sciatic nerve. The nerve was transected proximal to the bifurcation, The nerve ends were drawn 1 mm into a 17 mm silicone conduit and secured with 9/0 ETHILON™ Nylon Suture to create a critical gap defect of 15 mm. The conduit was filled with either nerve specific (NS)-ECM hydrogel or left empty. The ECM was prepared from a canine source. Two minutes were allowed for hydrogel formation and the muscle and skin layers were closed.

Regenerating nerve gaps were excised at 21 days, inspected grossly and fixed for immunohistochemistry. Gaps filled with NS-ECM showed improved axonal regrowth from the proximal nerve stump compared to empty conduits both grossly (FIG. 6) and on immunohistochemical section.

These data support the ability of NS-ECM to bridge critical gaps in peripheral nerves.

Example 3—Nerve-Specific Extracellular Matrix Hydrogel Promotes Recovery Following Reconstruction of the Recurrent Laryngeal Nerve 1. Summary Damage to the nerves that innervate the larynx, in particular the recurrent laryngeal nerve (RLn) can result in severe consequences for patients. Permanent RLn impairment may significantly impact quality of life by increasing vocal effort and reducing voice quality, and in some patients the condition can become life threatening. A number of clinical solutions exist, however functional recovery following these procedures is slow and often incomplete. Therefore, methods that accelerate or improve re-innervation following reconstruction of the RLn are of significant clinical interest. This example describes the production, characterization and use of an injectable, peripheral nerve-specific extracellular matrix (NS-ECM) based hydrogel to improve outcomes following reconstruction of the RLn. The hydrogel was tested in a canine model of RLn transection and anastimos. The anastimos was enclosed by a silicon conduit and either left empty or injected with either a NS-ECM hydrogel or a non-nerve-specific extracellular matrix, urinary bladder matrix (UBM) hydrogel. After 6 months, both NS-ECM and UBM significantly increased the amplitude of stimulation reaching the vocalis muscle (0.744 mV and 0.719 mV respectively) compared to the conduit alone (0.343 mV). Afterwards, the posterior cricoarytenoid muscle was harvested and muscle fiber diameter was measured. Differences between the control and treatment groups (NS-ECM and UBM) are small but significant, e.g., 53.5 μm compared to 58.4 μm and 61.7 μm, respectively. These results show that the NS-ECM hydrogel can provide supportive scaffolding to promote in vivo axonal repair of the RLn.

2. Materials and Methods 2.1. Preparation of Peripheral Nerve ECM

Equine sciatic nerve was harvested following euthanasia of adult animals for reasons unrelated to nerve injury or neurological disease. The tissue was then frozen for at least 16 h at −80° C. The epineurium was stripped and the tissue was sectioned longitudinally and cut into lengths of <5 cm. Decellularization was performed as described in Example 1.

2.2. Confirmation of Decellularization

Qualitative assessment of DNA content was performed using immuno fluorescence staining. Fixation of lyophilized ECM scaffolds was performed in 10% formalin. Samples were embedded in paraffin, sectioned, and stained with H&E or with DAPI to verify removal of nuclei. Additional samples were stained using Luxol™ fast blue (registered trademark of Rohm and Haas Co.) to determine removal of myelin. Qualitative assessment of DNA content was conducted by digesting the ECM scaffold in 0.1 mg/mL proteinase K solution. The protein was removed by repeated Trizol extraction and centrifugation (10,000 G) until no white precipitation (protein) was observed at the interface while the aqueous layer extract was mixed with 3 M sodium acetate and 100% ethanol. The solution was frozen using dried ice and centrifuged to produce a DNA pellet. The pellet was rinsed with 70% ethanol, centrifuged (10,000 G), and dried. Double-stranded DNA was quantified using PicoGreen following kit instructions.

2.3 Assessment of Scaffold Architecture

Scaffold architecture was assessed by scanning electron microscopy (SEM), histologic staining, and immunolabeling. For SEM, lyophilized samples were fixed in cold 2.5% (v/v) glutaraldehyde in PBS for at least 24 h, followed by three washes in PBS. Lipid fixation was performed in 1% (w/v) osmium tetroxide (Electron Microscopy Sciences) for 1 h followed by three washes in PBS. Fixed samples were then dehydrated using a graded series of ethanol-water solutions (30%-100%) followed by 15 min in hexamethyldisylizane and subsequent air-drying. The dried samples were mounted onto aluminum stubs and sputter coated with a 3.5 nm layer of gold-palladium alloy using a Sputter Coater 108 Auto (Cressington Scientific Instruments). Images were taken with a scanning electron microscope (JEOL JSM6330f).

For histologic analysis, scaffold materials were fixed in 10% neutral buffered formalin, embedded in paraffin and sectioned at 5 μm. Samples were dewaxed using xylenes and a graded series of ethanol washes (100-70%) then stained using hematoxylin and eosin. Stained samples were dehydrated using the reverse of the procedure above, coverslipped, and viewed under a light microscope (Nikon e600).

Immunolabeling was performed with antibodies specific to ECM components indicative of the neuronal basal lamina (collagen IV and laminin) and more general connective components (collagen I and III). Briefly, after deparaffination, all slides were subjected to antigen retrieval by immersion in 95° C.-100° C. in citric acid solution (10 mM, pH 6.0; 20 min) followed by rinsing in a 1×Tris buffered saline/Tween-20 solution (0.1% Tween 20 v/v, pH 7.4; 3 washes, 5 min each). Samples were then washed in PBS and treated with a pepsin digestion (0.05% pepsin w/v in 10 mM HCl) solution for further antigen retrieval. Samples were blocked against nonspecific binding using a solution consisting of 2% horse serum, 1% bovine serum albumin, 0.1% Tween-20, and 0.1% Triton X-100 in PBS for 30 min at room temperature. Primary antibodies were diluted in the blocking solution and applied to sections overnight at 4° C. Antibodies to collagen I, III, and IV (Sigma) were used at a concentration of 1/200. Samples were washed in PBS and appropriate fluorescently labeled secondary antibodies (AlexaFluor 488) were applied for 30 min at room temperature. All secondary antibodies were diluted 1:250 in the blocking solution. Slides were washed in PBS and coverslipped in the aqueous mounting medium before observation under a fluorescent microscope (Nikon e600).

2.4 Generation of Enzymatic Degradation Products

Enzymatic degradation products were generated as described in Example 1.

2.5 Evaluation of Effects of Enzymatic Degradation Products Upon Neurite Outgrowth Spinal cord neurons were isolated from embryonic day 14 Sprague-Dawley rat pups. Spinal cords were collected in cold Hanks' buffered salt solution without $Ca^{2+}$ and $Mg^{2+}$ (14 170-112, Gibco, Carlsbad, Calif., USA), minced into pieces approximately 0.5 mm in size and enzymatically dissociated in 2 ml 0.25% trypsin solution containing 0.05% collagenase L1 (MP Biomedicals, Solon, Ohio, USA) at 37° C. for 20 min. Cell digestion was inhibited by adding 2 ml SBTI-DNAse solution (0.52 mg/ml soybean trypsin inhibitor, T-9003; 3.0 mg/ml BSA, A-2153; 0.04 mg/ml bovine pancreas DNAse, D-4263; Sigma). The cell suspension was gently triturated and centrifuged at 800×g for 5 min. The resulting pellet was then resuspended in plating medium and gently triturated. The plating medium consisted of 20% horse serum (16 050-130, Gibco), (25 030-081, Gibco), 5 ml HBSS without $Ca^{2+}$ and $Mg^{2+}$ (14 170-112, Gibco) and 9.8 ml Dulbecco's modified Eagle's medium with L-glutamine (DMEM; D5648, Sigma). All non-dispersed tissue was allowed to settle before being discarded. Spinal cord neurons were seeded on poly-L-lysine-coated coverslips (12.5 μg/ml in $H_2O$; P1274, Sigma) in plating medium at a plating density of 3×105 cells/mL and allowed to adhere for 4 h in culture conditions of 5% $CO_2$ and 37° C. After 4 h, the medium was exchanged with 1 ml serum-free culture medium containing Neurobasal-A (NBA, 10 888-022, Gibco), and 1 mM Glutamax (35 050-061, Gibco). As a positive control, 1×B27 supplement was added to the media. The cells were maintained in a humidified 5% $CO_2$ atmosphere at 37° C., with 50% of the culture medium changed every 4 days. Three images at 20× magnification were taken per well. The number of cells with neurite extensions and the length of neurite extensions were counted using NeuronJ (ImageJ, NIH).

2.6 Formation of Hydrogel from Enzymatic Degradation Products

Gelation was induced by adjusting the pH of the pepsin digest to 7.4 using 0.1M NaOH and PBS. Neutralization was accomplished by the addition of one-tenth the digest volume of 0.1 N NaOH, one-ninth the digest volume of 10×PBS, and then diluting to the desired final ECM concentration. Concentrations between 8 and 15 mg/mL were examined for their ability to form a hydrogel. Dilutions were performed on ice and ECM pre-gel was cast into a stainless steel ring within a 6 well cell culture cluster. The gel solution was placed in a non-humidified 37° C. and allowed to gel for 1 h. Resultant hydrogels were then investigated using SEM as described above.

2.7 Evaluation of Hydrogel Cellular Compatibility

N1E-115 mouse neuroblastoma cells (ATCC No. CRL 2263), were cultured in DMEM (Sigma) with 10% fetal bovine serum (FBS; Thermo Fisher Scientific, Waltham Mass., USA)/1% pen/strep (Sigma) in T-75 flasks. N1E-115 cells in DMEM with 2.5% FBS/1% pen strep were seeded at a concentration of 8,500 cells on the surface of a 6 mg/mL nerve ECM or UBM-ECM gel in a 96 well plate. Wells seeded with cells in a media containing pepsin digest instead of ECM digest were used as controls. Following 18-24 hrs in culture with ECM, 2 μM calcein-AM and 2 μM ethidium homodimer-1 was added to each well to evaluate cytotoxicity. Membrane-permeable calcein-AM, but not ethidium homodimer-1, is hydrolyzed in live cells that fluoresce in green and dead cells that bind and activate ethidium homodimer-1, but not calcein-AM, fluoresce in red.

2.8 Animal Anesthesic and Surgical Procedures 2.8.1 Ethics Statement

This study was performed in accordance with the PHS Policy on Humane Care and Use of Laboratory Animals, the NIH guide for Care and Use of Laboratory Animals, federal and state regulations, and was approved by the Cornell University Institutional Animal Care and Use Committee (IACUC). Animals were brought into the research unit and given a 7 day acclimatization period prior to any procedure. Daily record logs of medical procedures were maintained. Cages with elevated floors were cleaned daily and disinfected biweekly. The animals were fed twice a day to maintain proper body condition, and allowed water ad libitum. Group housing provided socialization and ample space for exercise.

2.8.2 Animals and Instrumentation

Eleven female Beagle dogs (age 5-7 years, body weight 6.8±0.7 kg, range 6.4-8.7 kg) with no history of upper airway disease and normal laryngeal function, determined endoscopically, were used. Dogs were chosen at random and fasted for at least six hours before anesthesthetic procedures. At the conclusion of each procedure, dogs were monitored for one hour before returning to their group housing.

After fasting overnight, each dog was anesthetized with dexmedatomidine (2 mcg/kg IV followed by 2 mcg/kg/hour) and maintained under anesthesia at a constant expired isoflurane concentration (approximately 1MAC, 1.3%). Monitoring consisted of continuous electrocardiogram, pulse oximetry, non-invasive blood pressure, capnography and temperature.

Analgesia was provided with pre-operative Meloxicam (0.2 mg/kg body weight) subcutaneously (SQ), followed by meloxicam given as an oral suspension (0.1 mg/kg body weight), daily for four additional days.

2.8.3 Surgery

Animals were placed in left lateral recumbency and a lateral approach to the larynx was made in a standard fashion anterior to the right linguofacial vein, the subcutaneous fascia was divided and the main trunk of the right Recurrent Laryngeal nerve (RLn) identified. The RLn was identified and transected 15 mm inferior to the cricoid. These experiments were performed on the right side of the larynx as there is evidence for reduced functional recovery of left RLn injury compared to right (Woodson (2008)). Endoscopy using a rigid endoscope (2.7 mm diameter, Olympus) was performed to verify right sided paralysis immediately after surgery.

2.8.4 Experimental Groups

Animals were randomly (computer generated code) divided into three groups. In the control group, RLn transection was immediately followed by end-end RLn-RLn anastomosis performed using 3-5 epineural stitches of nylon 9-0 suture. Care was taken to avoid driving the needle or suture through the nerve fascicles. The anastomosis was surrounded by a preplaced empty 7 mm silicone conduit (3.5 mm internal diameter, Silastic; Dow Corning, Midland, Mich.) tagged to the perineurium at either end. In the two treatment groups the conduit was filled with either ECM derived from equine motor nerve (NS-ECM); or with ECM derived from Urinary Bladder Matrix (UBM) and introduced into the conduit lumen via an 18 gauge needle. Hydrogels were brought to room temperature 5 minutes prior to injection into the conduit. The incision was then closed in layers.

Animals were euthanized at 6 months following implantation and laryngeal muscles and nerves harvested bilaterally for histology and immunohistochemistry.

2.8.5 Endoscopy

Endoscopy using a rigid endoscope (2.7 mm diameter, Olympus) immediately following surgery, and at 2 and 6 months to assess arytenoid movement under light sedation (dexmedetomidine (1 mcg/kgIV), Jansson (2000); Ducharme (2010)).

2.8.6 Evoked CMAP Detection

Immediately prior to euthanasia, animals were anesthetized and anesthesia was maintained with isofluorane in $O_2$ via an endotracheal tube capable of detecting evoked compound motor action potentials (CMAP) from the vocalis muscle following proximal stimulation of the recurrent laryngeal nerve (NIM EMG Endotracheal tube, (inner diameter 7.0 mm, outer diameter 10.5 mm) Medtronic) (Dralle (2008)).

The right RLn was exposed by dissection in the mid cervical region and a single monopolar needle (Neuroline monopolar, AMBO Inc.) placed adjacent to the RLn 10 cm caudal to the anterior ring of the cricoid cartilage. A supramaximal pulse (8-14 mA) was applied to the monopolar needle and the corresponding CMAP recorded at the vocalis muscle (Sierra Wave II, Caldwell Laboratories, Kennewick, Wash.). Presence/absence and peak amplitude of each CMAP was recorded for each of three repetitions. This procedure was repeated on the left side.

Endoscopy was performed during the same anesthetic episode and the degree of arytenoid abduction at peak inspiration determined under light sedation (Jansson (2000); Ducharme (2010)).

2.8.7 Immunohistochemistry—Muscle

Posterior cricoarytenoid (PCA) and lateral cricoarytenoid (LCA) muscles were harvested from explanted larynges and weighed. Collagen V immunonohistochemistry was performed on mid sections of left and right PCA and LCA muscles and minimum fiber (Feret's) diameters determined using custom semi-automated software written in Matlab. 8 μm-thick cryosections of acetone-fixed muscle were used for immunohistochemical analysis. Cryosections were washed with phosphate buffered saline containing 0.05% Tween 20 (PBST) for 3 times (5 min each). Nonspecific staining was blocked with a mixture of 10% rabbit serum and 2×casein for 30 minutes at room temperature. The primary antibody goat anti-type V collagen antibody (SouthernBiotech, Birmingham, Ala.) was diluted to 1:1,000 in PBS containing 1×casein, and the sections were incubated for 1.5 hr at 37° C. Biotinylated rabbit anti-goat IgG (Vector Laboratories, Burlingame, Calif.) was diluted to 1:200 in PBS, and incubated for 30 min at room temperature. Finally, streptavidin-Texas Red (Molecular Probe, Life Technologies, Grand Island, N.Y.) was used to visualize positive staining (used at 1:200 in PBS), and then the sections were mounted in Vectashield containing Dapi (Vector Laboratories). PBST was used for washing throughout the procedure. Goat IgG was diluted to the same final concentration as primary antibody was used as a negative control. IHC results were examined and photographed using Olympus AX 70 compound microscope.

2.8.8 Histomorphologic Examination—Nerve

Cross-sections were obtained 5 mm proximal and 5 mm distal to the anastomosis, stained with azur 2-methylene blue-safranin and total number of axons, percentage of myelinated axons, number of fascicles and the number of axons in the largest fascicle delineated using semi-automated software (Volocity). Axon number was divided by the area sampled to calculate average myelinated axon density. Samples were stained also with hematoxylin and eosin for histomorphologic examination.

2.8.9 Data Analysis

Raw CMAP data was exported as a text file and analyzed using custom software written in MATLAB to determine peak amplitude and area of the CMAP. Mean values were determined from the three CMAPs recorded on each side. For each parameter, differences between left and right CMAPs was determined using Wilcoxon-signed rank tests.

3. Results 3.1 Confirmation of Decellularization

Effective decellularization of ECM based biomaterials is essential to remove the majority of immunogenic cellular constituents while leaving the tissue-specific structural and functional components intact and promoting an appropriate regenerative response (Brown (2013), Crapo (2011)). A nerve-specific decellularization protocol was used to decellularize equine sciatic nerve (Medberry (2013)). The NS-ECM generated was then fully characterized.

Figure 7A:
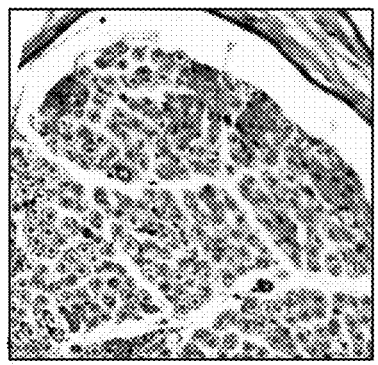
Figure 7B:
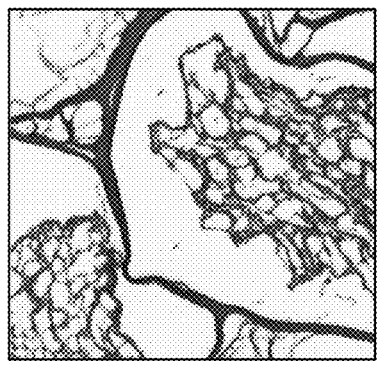
Figure 7C:
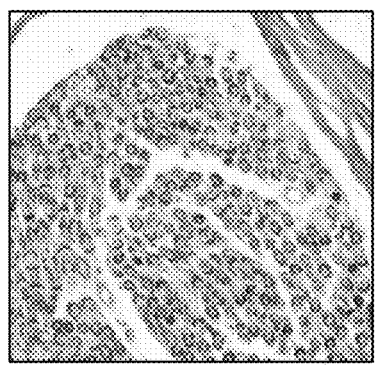
Figure 7D:
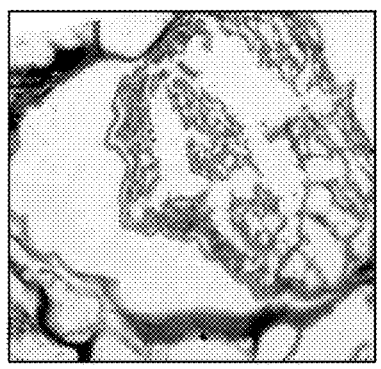
Figure 7E:
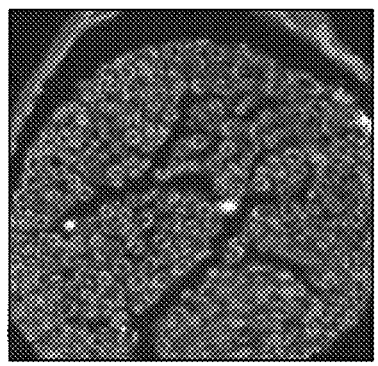
Figure 7F:
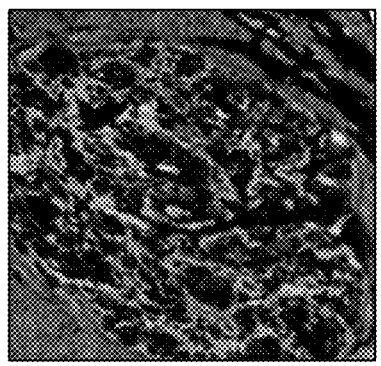
Figure 7G:
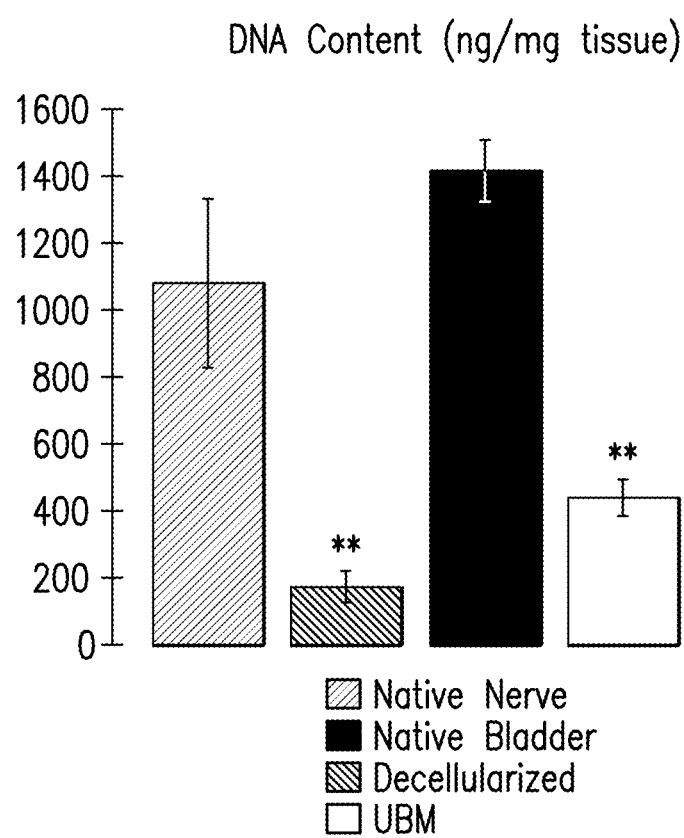

Following decellularization, no nuclei were visible in hematoxylin and eosin (H&E) stained sections under light microscopy (FIGS. 7A and 7B). In some samples, a small number of nuclei (2-3 nuclei/40× field) were observed when labeled with DAPI (FIGS. 7C and 7D). When present, retained nuclei were observed within the inner most bundles of the treated tissues. Myelin, a potentially immunogenic axonal component, was removed effectively by the decellularization process (FIGS. 7E and 7F, Luxol® fast blue).

dsDNA content was significantly decreased by approximately 85% in the decellularized tissue (158.1±34.5 ng/mg) was compared to native tissue (1,043.65±291.20 ng/mg (FIG. 7G, Quantitative PicoGreen assay). These values are consistent with those reported for multiple FDA approved, commercially available ECM scaffold materials (Gilbert (2009)). Results were compared to those obtained for an ECM material derived from urinary bladder, prepared as reported in Brown (2006), for comparison.

3.2 Maintenance of Extracellular Matrix Ultrastructure and Components

The maintenance of nerve-specific structural and functional components was investigated using electron microscopy, immunofluorescent labeling, and biochemical assays. Decellularized sciatic nerves were characterized under scanning electron microscopy (SEM) by an ultrastructure similar to that of native tissue (FIG. 8A-D). In cross section, distinct nerve bundles were observed, with intact epineureum and a dense, intact perineurium surrounding each individual nerve bundle. The epineurium was less dense and larger pores are were observed than in the native tissue. A number of individual reticular fibers were also observed. These larger and smaller fibers likely represent the collagen I and III which comprise the majority of the extracellular matrix of the native epineurium. The architecture of the endoneurium was retained but no longer contained individual nerve fibers (FIG. 8G-J).

Organization of collagen I, III, and IV within the decellularized tissues was similar to that of native nerve tissue (FIG. 8E-J). Although some structural components were disrupted, the basal lamina was strongly preserved as evidenced by the distribution of collagen IV (a major constituent of the basal lamina) within the decellularized samples. Collagen IV was present both within the endoneurial basal lamina and within the perineurium. The intensity of the staining within the endoneurium, however, was less and the architecture slightly disrupted as compared to native tissue.

Biochemical testing was performed to assess the quantity of basic ECM components including hydroxyproline and glycosaminglycans (GAG) as well as for nerve-specific growth factors including ciliary neurotrophic factor (CNTF) and nerve growth factor (NGF). The decellularization process increased the hydroxyproline concentration from 34.9±9.1 ug/mg in native tissue to 65.0±9.4 ug/mg in NS-ECM (FIG. 8K). This enrichment of hydroxyproline content was likely a consequence of removal of other components of the ECM. Conversely, only 60% of initial GAG content was preserved (native 51.3±8.0 ug/mg to 31.0±16.7 ug/mg) (FIG. 8M). Enzyme-linked immunosorbent assay (ELISA) showed that 26% and 50% of the native levels of NGF (native 680.9 pg NGF/g tissue±160.8 pg/g; NS-ECM 177.0 pg NGF/g ECM±33.2 pg/g) and CNTF, respectively, were conserved in the nerve ECM scaffold (FIGS. 8L and 8N). Despite a non-nerve tissue origin, similar levels of NGF (161.0 pg NGF/g UBM±38.5 pg/g) and CNTF were found in the UBM scaffold ((FIGS. 8L and 8N; and results were similar to those previously reported for UBM.

3.3 Bioactivity of Degradation Products

The degradation products of ECM based scaffold materials derived from decellularization of multiple tissues possess bioactivity including the ability to promote chemotaxis, proliferation and cell differentiation. Once decellularized, NS-ECM was degraded for processing into a hydrogel as described in Medberry (2013). Briefly, NS-ECM was milled into a powder and digested in a solution of 1 mg/mL pepsin in 0.01 M HCl. The digest solution was then neutralized using 0.1 M NaOH, 10× and 1×PBS at varying concentrations.

Bioactivity of the degradation products were analyzed through a neurite outgrowth assay. Primary spinal cord neurons were harvested from E14 Sprague-Dawley rat embryos. Cells were then plated and media supplemented with a range of concentrations of NS-ECM and UBM digests (125, 250, 500 ng/mL). Neurite outgrowth was assessed at time points 1, 2, and 4 days post-plating using an ImageJ based algorithm as previously reported. Results were compared to media supplemented with a neuron survival and growth supplement (B27, positive control), media alone (negative control), or media containing neutralized pepsin at a concentration equal to that of the digested ECM treatment groups (FIG. 9A-D). A dose dependent increase in neurite outgrowth was observed at all time points with increasing neurite outgrowth observed to correspond to increasing ECM supplementation.

3.4 Formation of Injectable Hydrogel

The decellularized tissue has been enzymatically digested and those nerve-specific degradation products were found to promote neuronal outgrowth. Those same degradation peptides can be formed into a thermally-sensitive hydrogel. The pepsin digest spontaneously polymerized at neutral pH and body temperature. The ability of this material to gel at various concentrations was investigated. It was found that the digest formed a loose gel as low as 8 mg/mL. The gel was more firm the more concentrated it was prepared. The decellularized tissue was enzymatically digested using pepsin under acidic conditions. The decellularized nerve was formed into a hydrogel which spontaneously polymerized at neutral pH and body temperature at a concentration between 8 mg/ml and 15 mg/ml (FIG. 4A-D).

Fiber length was measured by analyzing SEM images at 3000-4000 times magnification using Image J. Approximate fiber end-to-end lengths were found to be 10-16 micons on average (12.1 um±3.5 um). Individual pores were isolated and their diameters were measured using ImageJ software. Pores were randomly distributed throughout the gel and possessed average pore diameter of 2.23±1.46 um microns.

3.5 Restoration of Nerve Function Following Reconstruction of the RLn

Following characterization of the decellularized NS-ECM and corresponding nerve-specific hydrogel, a pilot study evaluating the effects of NS-ECM on anastomosis of the recurrent laryngeal nerve was performed. A canine preclinical model of laryngeal nerve injury, a widely accepted preclinical animal model of human laryngeal disease (Sanders (1993), Kim (2004)), was used.

The right recurrent laryngeal nerve was transected and immediately anastomosed, the anastomosis was surrounded by a silicone conduit and filled with either NS-ECM or UBM hydrogel (15 mg/ml, FIG. 10A) or left empty (control).

Surgical implantation was straightforward with rapid gelling of both hydrogels within the conduit.

Six months after implantation, laryngeal endoscopy revealed arytenoid movement but ineffective abduction, due to synkinetic reinnervation following anastomosis of the common RLn trunk. Under a terminal anesthetic episode, motor action potential conduction across the anastomosis site was determined using supramaximal Rln proximal stimulation and Compound Motor Action Potential (CMAP) recording at the vocalis muscle (FIG. 10C)

Figure 10A:
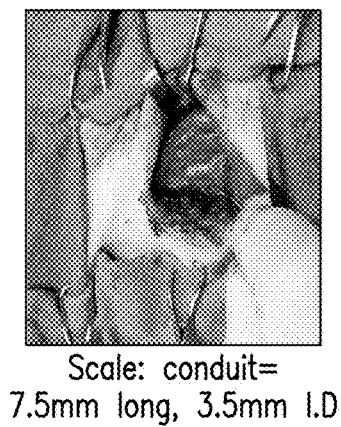
Figure 10B:
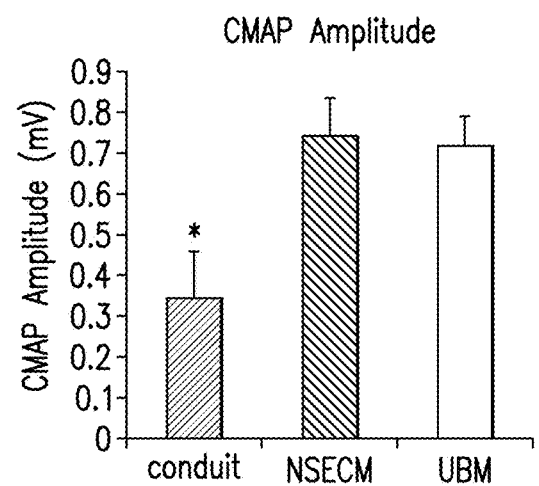
Figure 10C:
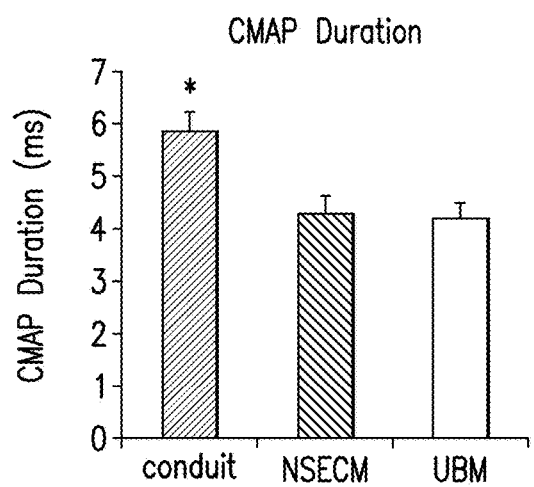

Both NS-ECM and UBM significantly increased the amplitude of stimulation reaching the vocalis muscle (0.744 mV and 0.719 mV respectively) compared to the conduit alone (0.343 mV) (FIG. 10B).

Figure 10D:
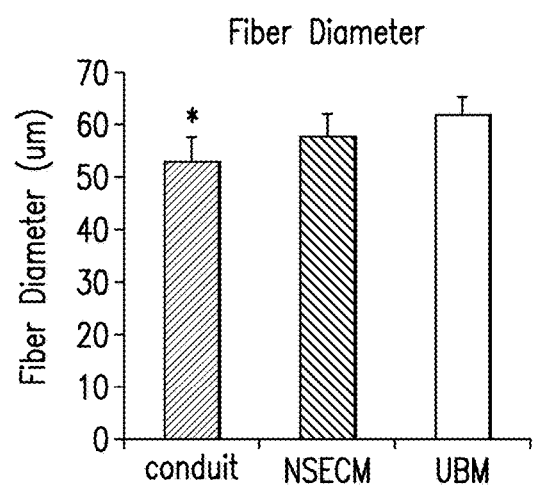

Minimum Fiber diameter was increased in the NSECM and UBM groups compared to controls in collagen V immuno-labelled right posterior cricoarytenoid (PCA) muscles (FIG. 10D). Differences between the control and treatment groups (NS-ECM and UBM) are small but significant, 53.5 µm compared to 58.4 µm and 61.7 µm respectively. Together these data suggest that NS-ECM and UBM hydrogels improve nerve repair with anastomosis.

4. Discussion 4.1 Effective Decellularization

Decellularization of xenogeneic tissue offers a number of potential benefits: the minimization of immunogenic reactions that would lead to graft rejection, the provision of an optimized biomaterial without competing donor cells, and a reduced risk of disease transmission. However, any processing step intended to remove cells will alter the native three-dimension architecture of the ECM to some degree. Therefore it is generally desirable to use the mildest protocol possible that yields an acellular material with the least disruption to the structural and functional components of the ECM. The decellularization method used in this Example produced an 85% decrease in DNA content when compared to native tissue (85%; 158.1±34.5 ng/mg, 1,043.65±291.20 ng/mg).

The above-presented results demonstrate effective generation of NS-ECM hydrogel, and that NS-ECM hydrogel retains microarchitecture and promotes dose-dependent neurite extension (bioactive). The results also show that NS-ECM is a practical solution for supporting nerve repair, e.g., gels rapidly (within 60 seconds) and is readily injected into conduit at site of injury.

4.2 Determination of Reinnervation of the Vocalis Muscle Using the Above-Described Method Supramaximal proximal nerve stimulation and recording of a compound motor action potential at the vocalis muscle allows quantification of reinnervation across the anastomosis site. Reinnervation of the thyroarytenoid complex is crucial to the restoration of vocal cord function and voice. Although posterior cricoarytenoid muscle fiber diameters were increased in both treated groups, functional recover was poor with un-coordinated arytenoid movement and little abduction was achieved. This result is expected with repair to the common trunk of the RLn in which abductor and adductor fibers are spatially intermingled (Crumley (2000), Benjamin (2003), Zealear (2006)).

Manipulation of the microenvironment at the site of nerve injury promotes improved repair. An inert but non-absorbable silicone conduit was used in this Example to maintain this microenvironment. Multiple interventions have been shown to improve axonal regrowth in rodent models, however, the translation to clinical therapies in human patients has been slow. A preclinical large animal model of laryngeal nerve injury was used in this Example to assess NS-ECM.

One of the advantages of this approach is that nerve regrowth in large animal models is slower and less regenerative than in rodent systems. Even the gold standard of care for nerve gap defects, the autologous nerve graft is associated with various clinical complications, including donor site morbidity, limited availability, nerve site mismatch, and the formation of neuromas.

Scaffold based approaches using individual extracellular matrix proteins such as keratin, collagen and fibronectin have also been shown to support axonal regrowth (Hill (2011); Madison (1985); Madison (1988); Toba (2001); Lee (2006); Sierpinski (2008a)) and enhance Schwann cell function (Sierpinski (2008b)). Here, the complete milieu of NS-ECM products to promote repair was recruited.

The ECM is the framework including both structural and functional proteins that provides the environment that cells live in. The ECM provides cues for cell attachment, migration, and proliferation but also is manipulated by resident cells. This dynamic interaction between ECM and cells is key for tissue development and homeostasis. Because of these important functions, biological scaffolds composed of ECM have been used in a wide variety of tissue engineering and regenerative medicine applications, including ventral hernia repair, musculotendinous tissue reconstruction, dura mater replacement, reconstructive breast surgery, pelvic floor reconstruction, and the treatment of cutaneous ulcers, among others. These materials act as inductive templates for the generation of new functional, site-appropriate tissue formation (Brown (2013); Badylak (2014)).

An inductive, ECM based scaffold approach was investigated as a solution to this problem. The advantage of using a decellularized tissue or ECM scaffold is that it promotes constructive remodeling by initially providing an acellular structure that degrades rapidly, releasing mitogenic and chemotactic proteins. These modulate the innate immune system to promote a friendly rather than destructive immune response. As a whole, it encourages the formation of new functional tissue (Sobotka (2011)).

ECM scaffolds derived through the decellularization of a wide array of tissues and organs have been successfully to treat injuries in variety of preclinical and clinical applications, including skeletal muscle, the esophagus, and lower urinary tract, among others (Wang (2011a)). Recent evidence suggests that ECM scaffolds derived from site-specific tissue can elicit a superior functional recovery in some applications (Wang (2011b)). The presence of a site specific advantage was investigated by comparing the peripheral nerve based scaffold used in this Example to urinary bladder matrix, which is a widely used biologic scaffold.

Not all of the proposed decellularization methods have been shown to be effective for removal of sufficient cellular content and maintenance of tissue structure, resulting in ineffective recovery in some studies. For this reason, histologic, immunologic, and quantitative methods was used to validate the decellularization process.

A peripheral nerve based hydrogel was derived, characterized and tested in a canine model of laryngeal nerve transection and reconstruction in this Example. A peripheral nerve was decellularized maintaining peripheral NS-ECM components, including nerve specific growth factors. The decellularized tissue was enzymatically digested into a mixture of degradation peptides. That mixture of peptides was found to be bioactive and to promote neurite outgrowth. The peptide mixture was then formed into a hydrogel and injected into a clinically relevant model of nerve transection. It was found that the NS-ECM hydrogel improves recovery with anastomosis.

Example 4

Animals as described in Example 3 were anesthetized and placed in left lateral recumbency and a lateral approach to the larynx was made in a standard fashion anterior to the right linguofacial vein. The subcutaneous fascia was divided and the main trunk of the right RLn was identified. The RLn was identified and transected 15 mm inferior to the cricoid. The incisions were then closed in layers and animals were allowed to develop chronic denervation of the RLn for three months. After three months, the animals were again anesthetized as described above and a nerve graft was performed. The cervical nerve was grafted to the recurrent laryngeal nerve by anastomosis of the two ends of each nerve. The anastomosis was surrounded by a preplaced empty 7 mm silicone conduit (3.5 mm internal diameter, Silastic; Dow Corning, Midland, Mich.) tagged to the perineurium at either end. As shown in FIG. 11, in the treatment group, the conduit was filled with ECM derived from equine motor nerve (NS-ECM introduced into the conduit lumen via an 18 gauge needle). Hydrogels were brought to room temperature 5 minutes prior to injection into the conduit. The incision was then closed in layers.

These data demonstrate that NS-ECM can be used to support nerve grafting either soon after injury (acute) or after a period of delay (chronic).

7. REFERENCES

1. Nagao R J, Lundy S, Khaing Z Z, Schmidt C E., Neurol Res. 2011 July; 33(6):600-8
2. Hudson T W, Zawko S, Deister C, Lundy S, Hu C Y, Lee K, Schmidt C E, Tissue Eng. 2004 November-December; 10(11-12):1641-51.
3. Hudson T W, Liu S Y, Schmidt C E. Tissue Eng. 2004 September-October; 10(9-10):1346-58.
4. Medberry C J, Crapo P M, Siu B F, Carruthers C A, Wolf M T, Nagarkar S P, Agrawal V, Jones K E, Kelly J, Johnson S A, Velankar S S, Watkins S C, Modo M, Badylak S F., Biomaterials. 2013 January; 34(4):1033-40.
5. Crapo P M, Medberry C J, Reing J E, Tottey S, van der Merwe Y, Jones K E, Badylak S F., Biomaterials. 2012 May; 33(13):3539-47.
6. Wolf M T, Daly K A, Brennan-Pierce E P, Johnson S A, Carruthers C A, D'Amore A, Nagarkar S P, Velankar S S, Badylak S F., Biomaterials. 2012 October; 33(29):7028-38.
7. U.S. Pat. No. 8,361,503 B2
8. PCT/US2012/045682
9. Brown B N, Badylak S F. Extracellular matrix as an inductive scaffold for functional tissue reconstruction. Transl Res. 2013 Nov. 8. pii: S1931-5244(13)00382-4.
10. Badylak S F. Decellularized Allogeneic and Xenogeneic Tissue as a Bioscaffold for Regenerative Medicine: Factors that Influence the Host Response. Ann Biomed Eng. 2014 Jan. 9. [Epub ahead of print]
11. Nichols, C. M., Brenner, M. J., Fox, I. K., Tung, T. H., Hunter, D. A., Rickman, S. R. & Mackinnon, S. E. Effects of motor versus sensory nerve grafts on peripheral nerve regeneration. *Exp. Neurol.* 190, 347-355 (2004).
12. Lee, S. K. & Wolfe, S. W. Peripheral nerve injury and repair. *J. Am. Acad. Orthop. Surg.* 8, 243-252 (2000).
13. Mackinnon, S. E., Doolabh, V. B., Novak, C. B. & Trulock, E. P. Clinical outcome following nerve allograft transplantation. *Plast. Reconstr. Surg.* 107, 1419-1429 (2001).
14. Kingham, P. J., Birchall, M. A., Burt, R., Jones, A. & Terenghi, G. Reinnervation of laryngeal muscles: a study of changes in myosin heavy chain expression. *Muscle Nerve* 32, 761-766 (2005).
15. Wang, W., Chen, D., Chen, S., Li, D., Li, M., Xia, S. & Zheng, H. Laryngeal reinnervation using ansa cervicalis for thyroid surgery-related unilateral vocal fold paralysis: a long-term outcome analysis of 237 cases. *PLoS One* 6, e19128 (2011a). PMCID: PMC3084757.
16. Wang, W., Chen, S., Chen, D., Xia, S., Qiu, X., Liu, Y. & Zheng, H. Contralateral ansa cervicalis-to-recurrent laryngeal nerve anastomosis for unilateral vocal fold paralysis: A long-term outcome analysis of 56 cases. *Laryngoscope* 121, 1027-1034 (2011b).
17. Sobotka, S. & Mu, L. Force characteristics of the rat sternomastoid muscle reinnervated with end-to-end nerve repair. *J. Biomed. Biotechnol.* 2011, 173471 (2011). PMCID: PMC3238804.
18. Lorenz, R. R., Esclamado, R. M., Teker, A. M., Strome, M., Scharpf, J., Hicks, D., Milstein, C. & Lee, W. T. Ansa cervicalis-to-recurrent laryngeal nerve anastomosis for unilateral vocal fold paralysis: experience of a single institution. *Ann. Otol. Rhinol. Laryngol.* 117, 40-45 (2008).
19. Smith, M. E., Roy, N. & Stoddard, K. Ansa-RLN reinnervation for unilateral vocal fold paralysis in adolescents and young adults. *Int. J. Pediatr. Otorhinolaryngol.* 72, 1311-1316 (2008).
20. Aynehchi, B. B., McCoul, E. D. & Sundaram, K. Systematic review of laryngeal reinnervation techniques. *Otolaryngol. Head. Neck. Surg.* 143, 749-759 (2010).
21. Birchall, M. A., Lorenz, R. R., Berke, G. S., Genden, E. M., Haughey, B. H., Siemionow, M. & Strome, M. Laryngeal transplantation in 2005: a review. *Am. J. Transplant.* 6, 20-26 (2006).
22. Hill, P. S., Apel, P. J., Barnwell, J., Smith, T., Koman, L. A., Atala, A. & Van Dyke, M. Repair of peripheral nerve defects in rabbits using keratin hydrogel scaffolds. *Tissue Eng. Part A.* 17, 1499-1505 (2011).
23. Madison, R., Da Silva, C. F., Dikkes, P., Chiu, T. H. & Sidman, R. L. Increased rate of peripheral nerve regeneration using bioresorbable nerve guides and a laminin-containing gel. *Exp. Neurol.* 88, 767-772 (1985).
24. Madison, R. D., Da Silva, C. F. & Dikkes, P. Entubulation repair with protein additives increases the maximum nerve gap distance successfully bridged with tubular prostheses. *Brain Res.* 447, 325-334 (1988).
25. Toba, T., Nakamura, T., Shimizu, Y., Matsumoto, K., Ohnishi, K., Fukuda, S., Yoshitani, M., Ueda, H., Hori, Y. & Endo, K. Regeneration of canine peroneal nerve with the use of a polyglycolic acid-collagen tube filled with laminin-soaked collagen sponge: a comparative study of collagen sponge and collagen fibers as filling materials for nerve conduits. *J. Biomed. Mater. Res.* 58, 622-630 (2001).
26. Lee, D. Y., Choi, B. H., Park, J. H., Zhu, S. J., Kim, B. Y., Huh, J. Y., Lee, S. H., Jung, J. H. & Kim, S. H. Nerve regeneration with the use of a poly(l-lactide-co-glycolic acid)-coated collagen tube filled with collagen gel. *J. Craniomaxillofac. Surg.* 34, 50-56 (2006).
27. Sierpinski, P., Garrett, J., Ma, J., Apel, P., Klorig, D., Smith, T., Koman, L. A., Atala, A. & Van Dyke, M. The use of keratin biomaterials derived from human hair for the promotion of rapid regeneration of peripheral nerves. *Biomaterials* 29, 118-128 (2008a).
28. Sierpinski, P., Garrett, J., Ma, J., Apel, P., Klorig, D., Smith, T., Koman, L. A., Atala, A. & Van Dyke, M. The use of keratin biomaterials derived from human hair for the promotion of rapid regeneration of peripheral nerves. *Biomaterials* 29, 118-128 (2008b).
29. Sanders, I., Jacobs, I., Wu, B. L. & Biller, H. F. The three bellies of the canine posterior cricoarytenoid muscle: implications for understanding laryngeal function. *Laryngoscope* 103, 171-177 (1993).
30. Zealear, D. L., Billante, C. R., Chongkolwatana, C., Rho, Y. S., Hamdan, A. L. & Herzon, G. D. The effects of chronic electrical stimulation on laryngeal muscle physiology and histochemistry. *ORL J. Otorhinolaryngol. Relat. Spec.* 62, 81-86 (2000).
31. Broome, C., Burbidge, H. M. & Pfeiffer, D. U. Prevalence of laryngeal paresis in dogs undergoing general anaesthesia. *Aust. Vet. J.* 78, 769-772 (2000).
32. Woodson, G. E., Hughes, L. F. & Helfert, R. Quantitative assessment of laryngeal muscle morphology after recurrent laryngeal nerve injury: right vs. left differences. *Laryngoscope* 118, 1768-1770 (2008).
33. Jansson, N., Ducharme, N. G., Hackett, R. P. & Mohammed, H. O. An in vitro comparison of cordopexy, cordopexy and laryngoplasty, and laryngoplasty for treatment of equine laryngeal hemiplegia. *Vet. Surg.* 29, 326-334 (2000).
34. Ducharme, N. G., Cheetham, J., Sanders, I., Hermanson, J. W., Hackett, R. P., Soderholm, L. V. & Mitchell, L. M. Considerations for pacing of the cricoarytenoid dorsalis muscle by neuroprosthesis in horses. *Equine Vet. J.* 42, 534-540 (2010).
35. Goslin, K., Schreyer, D. J., Skene, J. H. & Banker, G. Changes in the distribution of GAP-43 during the development of neuronal polarity. *J. Neurosci.* 10, 588-602 (1990).
36. Triolo, D., Dina, G., Lorenzetti, I., Malaguti, M., Morana, P., Del Carro, U., Comi, G., Messing, A., Quattrini, A. & Previtali, S. C. Loss of glial fibrillary acidic protein (GFAP) impairs Schwann cell proliferation and delays nerve regeneration after damage. *J. Cell. Sci.* 119, 3981-3993 (2006).
37. Cheetham, J., Radcliffe, C. R., Ducharme, N. G., Sanders, I., Mu, L. & Hermanson, J. W. Neuroanatomy of the equine dorsal cricoarytenoid muscle: Surgical implications. *Equine Vet. J.* 40, 70-75 (2008).
38. Crumley, R. L. Laryngeal synkinesis revisited. *Ann. Otol. Rhinol. Laryngol.* 109, 365-371 (2000).
39. Affleck B D, Swartz K, Brennan J 2003 Surgical consideration and controversies in thyroid and parathyroid surgery. Otolaryngol Clin North Am 36:159-187Spector B C, Netterville J L, Billante C, Clary J, Reinisch L, Smith T L 2001 Quality-of-life assessment in patients with unilateral vocal cord paralysis. Otolaryngol Head Neck Surg 125:176-182
40. Laccourreye O, Crevier-Buchman L, Pacona R, Ageel M, Brasnu D 1999 Intracordal fat injection for aspiration after recurrent laryngeal nerve paralysis. Eur Arch Otoloaryngol 256:458-461
41. Negus V E 1929 The mechanism of the larynx. London: W. M. Heinemann Ltd.; 1-45
42. Wolf, M., Daly, K., Reing, J., & Badylak, S. (2012). Biologic scaffold composed of skeletal muscle extracellular matrix. *Biomaterials,* 33(10), 2916-25.
43. Sawkings, M., Bowen, W., Dhadda, P., Markides, H., Sidney, L., Taylor, A., & White, L. (2013). Hydrogels derived from demineralized and decellularized bone extracellular matrix. 9(8), 7865-73.
44. Badylak, S. (2011, October). *Regenerative medicine: Possibilities and potencial.* The singularity summit.
45. Dralle H. Intraoperative monitoring of the recurrent laryngeal nerve in thyroid surgery. World J Surg. 2008 32(7): 1358-1366.
46. Crapo P M, Gilbert T W, Badylak S F. An overview of tissue and whole organ decellularization processes. Biomaterials. 2011 April; 32(12):3233-43.
47. Gilbert T W, Freund J M, Badylak S F. Quantification of DNA in biologic scaffold materials. J Surg Res. 2009 March; 152(1):135-9.
48. Brown B, Lindberg K, Reing J, Stolz D B, Badylak S F. The basement membrane component of biologic scaffolds derived from extracellular matrix. Tissue Eng. 2006 March; 12(3):519-26.
49. Kim, M. J., Hunter, E. J. & Titze, I. R. Comparison of human, canine, and ovine laryngeal dimensions. *Ann. Otol. Rhinol. Laryngol.* 113, 60-68 (2004).
50. Benjamin, B. Vocal cord paralysis, synkinesis and vocal fold motion impairment. ANZ J Surg 73, 784-786 (2003).
51. Zealear, D. L. & Billante, C. R. In: Vocal Fold Paralysis (eds Sulica, L. & Blitzer, A.) 17-32 (Springer Berlin, Heidelberg, 2006).
52. Deal D N, Griffin J W, Hogan M V, Nerve conduits for nerve repair or reconstruction. *J Am Acad Orthop Surg.* 2012 February; 20(2):63-8.

Various references are cited herein, the contents of which are hereby incorporated by reference in their entireties.

We claim:
1. A hydrogel comprising a decellularized peripheral nerve scaffold that has been enzymatically degraded to form a hydrogel, wherein the hydrogel promotes peripheral nerve repair.
2. The hydrogel of claim 1, comprised in a conduit.
3. The hydrogel of claim 1, where the peripheral nerve is non-autologous to an intended recipient of the hydrogel.
4. The hydrogel of claim 3, where the peripheral nerve is from an organism that is the same species as the intended recipient.
5. The hydrogel of claim 3, where the peripheral nerve is from an organism that is not the same species as the intended recipient.

\* \* \* \* \*